United States Patent
Pevsner et al.

(10) Patent No.: US 10,544,461 B2
(45) Date of Patent: Jan. 28, 2020

(54) DIAGNOSTIC AND PROGNOSTIC TEST FOR STURGE-WEBER SYNDROME, KLIPPEL-TRENAUNAY-WEBER SYNDROME, AND PORT-WINE STAINS (PWSS)

(71) Applicants: THE JOHNS HOPKINS UNIVERSITY, Baltimore, MD (US); KENNEDY KRIEGER INSTITUTE, Baltimore, MD (US); DUKE UNIVERSITY, Durham, NC (US)

(72) Inventors: Jonathan Pevsner, Baltimore, MD (US); Anne Comi, Baltimore, MD (US); Douglas Marchuk, Chapel Hill, NC (US); Matthew Shirley, Baltimore, MD (US)

(73) Assignees: The Johns Hopkins University, Baltimore, MD (US); Kennedy Krieger Institute, Inc., Baltimore, MD (US); Duke University, Durham, NC (US)

( * ) Notice: Subject to any disclaimer, the term of this patent is extended or adjusted under 35 U.S.C. 154(b) by 198 days.

(21) Appl. No.: 14/784,720

(22) PCT Filed: Apr. 16, 2014

(86) PCT No.: PCT/US2014/034319
§ 371 (c)(1),
(2) Date: Oct. 15, 2015

(87) PCT Pub. No.: WO2014/172434
PCT Pub. Date: Oct. 23, 2014

(65) Prior Publication Data
US 2016/0237492 A1    Aug. 18, 2016

Related U.S. Application Data

(60) Provisional application No. 61/812,309, filed on Apr. 16, 2013.

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,391,904 A | 7/1983 | Litman et al. |
| 4,816,567 A | 3/1989 | Cabilly et al. |
| 5,034,506 A | 7/1991 | Summerton et al. |
| 5,210,015 A | 5/1993 | Gelfand et al. |
| 5,235,033 A | 8/1993 | Summerton et al. |
| 5,310,893 A | 5/1994 | Erlich et al. |
| 5,451,512 A | 9/1995 | Apple et al. |
| 5,468,613 A | 11/1995 | Erlich et al. |
| 5,487,972 A | 1/1996 | Gelfand et al. |
| 5,545,806 A | 8/1996 | Lonberg et al. |
| 5,545,807 A | 8/1996 | Surani et al. |
| 5,569,825 A | 10/1996 | Lonberg et al. |
| 5,604,099 A | 2/1997 | Erlich et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,804,375 A | 9/1998 | Gelfand et al. |
| 6,150,584 A | 11/2000 | Kucherlapati et al. |
| 6,673,843 B2 | 1/2004 | Arbiser |
| 2008/0020385 A1 | 1/2008 | Frey et al. |
| 2011/0070221 A1 | 3/2011 | Bastian et al. |

FOREIGN PATENT DOCUMENTS

WO    2001-88124 A2    11/2001

OTHER PUBLICATIONS

Van Raamsdonk et al; N Engl J Med, vol. 363, pp. 2191-2199, 2010.*
Yandell, et al., A probabilistic disease-gene finder for personal genomes. Genome Research 2011;21(9):1529-42.
Bystrykh, Generalized DNA Barcode Design Based on Hamming Codes. PLoS One 2012;7(5):e36852.
Li, et al., Fast and accurate short read alignment with Burrows-Wheeler transform. Bioinformatics 2009;25(14)1754-60.
Li, et al., The Sequence Alignment/Map format and SAMtools. Bioinformatics 2009;25(16):2078-9.
Sadedin, et al., Bpipe: a tool for running and managing bioinformatics pipelines. Bioinformatics 2012;28(11):1525-6.

(Continued)

*Primary Examiner* — Jehanne S Sitton
(74) *Attorney, Agent, or Firm* — Johns Hopkins Technology Ventures

(57) ABSTRACT

The present invention relates to the fields of neurological and skin disorders. More specifically, the present invention provides methods and compositions for diagnosing and prognosing Sturge-Weber Syndrome (SWS), Klippel-Trenaunay-Weber Syndrome (KTWS), and Port Wine Stains (PWS). In one embodiment, a method for prognosing or monitoring treatment of a patient with SWS, KTWS and/or PWS comprises the steps of (a) providing a sample from the patient undergoing treatment; (b) determining the number of alleles in the sample comprising at least one activating somatic mutation in the guanine nucleotide-binding protein G subunit alpha (GNAQ) gene or protein; (c) comparing the number of alleles comprising the at least one somatic mutation to the number of alleles comprising the somatic mutation from a patient sample provided prior to undergoing treatment; and (d) determining that the patient is improving if there is a decrease in the number of alleles comprising the at least one somatic mutation from the sample of step (a).

9 Claims, 4 Drawing Sheets
Specification includes a Sequence Listing.

(56) References Cited

OTHER PUBLICATIONS

Happle, Lethal genes surviving by mosaicism: a possible explanation for sporadic birth defects involving the skin. J Am Acad Dermatol 1987;16(4):899-906.
Van Raamsdonk, et al., Frequent somatic mutations of GNAQ in uveal melanoma and blue naevi. Nature 2009;457(7229):599-602.
Takasaki, A Novel G q/11-selective Inhibitor. Journal of Biological Chemistry 2004;279(46):47438-45.
Weinstein, et al., Activating mutations of the stimulatory G protein in the McCune-Albright syndrome. N Engl J Med 1991;325(24):1688-95.
Lindhurst, et al., A mosaic activating mutation in AKT1 associated with the Proteus syndrome. N Engl J Med 2011; 365: 611-619.
Populo, et al., Analysis of GNAQ mutations, proliferation and MAPK pathway activation in uveal melanomas. British Journal of Ophthalmology 2011;95(5):715-9.
Coleman, et al., Structures of active conformations of Gi alpha 1 and the mechanism of GTP hydrolysis. Science 1994;265(5177):1405-12.
Kimple, et al., Regulators of G-Protein Signaling and Their G Substrates: Promises and Challenges in Their Use as Drug Discovery Targets. Pharmacological Reviews 2011;63(3):728-49.
Berman, et al., GAIP and RGS4 are GTPase-activating proteins for the Gi subfamily of G protein alpha subunits. Cell 1996;86(3):445-52.
Van Raamsdonk, et al., Mutations in GNA11 in uveal melanoma. N Engl J Med 2010;363(23):2191-9.
Van Raamsdonk, et al., Effects of G-protein mutations on skin color. Nature Genetics 2004;36(9):961-8.
Kaijo, et al., Vascular effects of endothelin-1 in stage 21 chick embryos. Heart Vessels 1997;12(6):300-5.
Hepler, et al., RGS4 and GAIP are GTPase-activating proteins for Gq alpha and block activation of phospholipase C beta by gamma-thio-GTPGq alpha. Proc Natl Acad Sci USA 1997;94(2):428-32.
Zhou, et al., Detection of RASA1 mutations in patients with sporadic Sturge-Weber syndrome. Childs Nerv Syst. Apr. 2011;27(4):603-7.
Tanwar, et al., Sturge-Weber syndrome with congenital glaucoma and cytochrome P450 (CYP1B1) gene mutations. J Glaucoma. Aut. 2010;19(6):398-404.
Comi, et al., Increased fibronectin expression in sturge-weber syndrome fibroblasts and brain tissue. Pediatr Res. May 2003;53(5):762-9.
Kusters-Vandevelde, et al., Activating mutations of the GNAQ gene: a frequent event in primary melanocytic neoplasms of the central nervous system. Acta Neuropathol. Mar. 2010;119(3):317-23.
Vissers, et al., Klippel-Trenaunay syndrome and Sturge-Weber syndrome: variations on a theme? Eur J Dermatol 2003;13(3):238-41.
Gasparini, et al., Angiodysplasia with osteohypertrophy affecting the oromaxillofacial area: clinical findings. J Craniofac Surg 2001;12(5):485-9.
Greene, et al., Sturge-Weber Syndrome. J Craniofac Surg 2009;20(Suppl 1):617-21.
Ch'ng, et al., Facial port-wine stains—clinical stratification and risks of neuro-ocular involvement. J Plast Reconstr Aesthet Surg 2008;61(8):889-93.
Piram, et al., Sturge-Weber Syndrome in Patients with Facial Port-Wine Stain. Pediatric Dermatology 2011;29(1):32-7.
Comi, Update on Sturge—Weber Syndrome: Diagnosis, Treatment, Quantitative Measures, and Controversies. Lymphatic Research and Biology 2007;5(4):257-64.
Saunders, et al., Strelka: accurate somatic small-variant calling from sequenced tumor-normal sample pairs. Bioinformatics 28, 1811-1817, 2012.
Thomas-Sohl, et al., Sturge-Weber syndrome: a review. Pediatr Neural 30, 303-310, 2004.
Comi, A., "Update on sturge-weber syndrome: diagnosis, treatment, quantitative measures, and controversies", Lymphatic Research and Biology, (2007) vol. 5, No. 4, pp. 257-264.
Onken, M., et al., "Oncogenic mutations in GNAQ occur early in uveal malanoma", Investigative ophthalmology & Visual Science, Dec. 2008, vol. 49, No. 12, pp. 5230-5234.
Shirley, M., "Sturge-weber syndrome and port-wine stains caused by somatic mutation in GNAQ", The New England Journal of Medicine, (2013), vol. 368, No. 21, pp. 1971-1979.
Van Raamsdonk, C., et al., "Frequent somatic mutations of GNAQ in uveal melanoma and blue naevi", Nature (2009) vol. 457, pp. 599-603.
Zhou, Q., et al., Fibronectin: characterization of a somatic mutation in sturge-weber syndrome, Medical Hypotheses, (2009), vol. 73, pp. 199-200.
Smith, et al., Comparison of biosequences. Adv Appl Math 2: 482-489, 1981.
Needleman, et al., A General Method Applicable to the Search for Similarities in the Amino Acid Sequence of Two Proteins. J Mol Biol 48, 443-453, 1970.
Pearson, et al., Improved tools for biological sequence comparison. Proc Natl Acad Sci USA 85, 2444-2448, 1988.
Altschul, et al., Gapped BLAST and PSI-BLAST: a new generation of protein database search programs. Nucleic Acids Res 25, 3389-3402, 1997.
Altschul, et al., Basic local alignment search tool. J Mol Biol 215, 403-410, 1990.
Henikoff, et al., Amino acid substitution matrices from protein blocks. Proc Natl Acad Sci 89, 10915-10919, 1992.
Kostelny, et al., Formation of a bispecific antibody by the use of leucine zippers. J Immunol 148, 1547-1553, 1992.
Pack, et al., Miniantibodies: use of amphipathic helixes to produce functional, flexibly linked dimeric FV fragments with high avidity in *Escherichia coli*. Biochemistry 31, 1579-1584, 1992.
Holliger, et al., "Diabodies": small bivalent and bispecific antibody fragments. Proc Natl Acad Sci USA 90, 6444-6448, 1993.
Gruber, et al., Efficient tumor cell lysis mediated by a bispecific single chain antibody expressed in *Escherichia coli*. J Immunol 152, 5368-6374, 1994.
Zhu, et al., Remodeling domain interfaces to enhance heterodimer formation. Protein Sci 6, 781-788, 1997.
Hu, et al., Minibody: A novel engineered anti-carcinoembryonic antigen antibody fragment (single-chain Fv-CH3) which exhibits rapid, high-level targeting of xenografts. Cancer Res 56, 3055-3061, 1996.
Adams, et al., Highly Specific in Vivo Tumor Targeting by Monovalent and Divalent Forms of 741F8 Anti-c-erbB-2 Single-Chain Fv1. Cancer Res 53, 4026-4034, 1993.
McCartney, et al., Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides. PEDS 8, 301-314, 1995.
Huse, et al., Generation of a large combinatorial library of the immunoglobulin repertoire in phage lambda. Science 246, 1275-1281, 1989.
Ward, et al., Binding activities of a repertoire of single immunoglobulin variable domains secreted from *Escherichia coli*. Nature 341, 544-546, 1989.
Vaughan, et al., Human antibodies with sub-nanomolar affinities isolated from a large non-immunized phage display library. Nat Biotechnol 14, 309-314, 1996.
Jones, et al., Replacing the complementarity-determining regions in a human antibody with those from a mouse. Nature 321, 522-525, 1986.
Riechmann, et al., Reshaping human antibodies for therapy. Nature 332, 323-327, 1988.
Presta, et al., Antibody engineering. Curr Opin Struct Biol 2, 593-596, 1992.
Verhoeyen, et al., Reshaping human antibodies: grafting an antilysozyme activity. Science 239, 1534-1536, 1988.
McCaffety, et al., Phage antibodies: filamentous phage displaying antibody variable domains. Nature 348, 552-554, 1990.

(56) References Cited

OTHER PUBLICATIONS

Hoogenboom, et al., By-passing immunisation: Human antibodies from synthetic repertoires of germline VH gene segments rearranged in vitro. J Mol Biol 227, 381-388, 1992.
Marks, et al., By-passing immunization: Human antibodies from V-gene libraries displayed on phage. J Mol Biol 222, 581-597, 1991.
Boder, et al., Yeast surface display for screening combinatorial polypeptide libraries. Nat Biotechnol 15, 553-537, 1997.
Hanes, et al., In vitro selection and evolution of functional proteins by using ribosome display. Proc Natl Acad Sci USA 94, 4937-4942, 1997.
Jakobovits, Production and selection of antigen-specific fully human monoclonal antibodies from mice engineered with human Ig loci. Adv Drug Deliv Rev 31, 33-42, 1998.
Marks, et al., By-passing immunization: building high affinity human antibodies by chain shuffling. Biotechnology (NY) 10, 779-783, 1992.
Lonberg, et al., Antigen-specific human antibodies from mice comprising four distinct genetic modifications. Nature 368, 856-859, 1994.
Morrison, Success in specification. Nature 368, 812-813, 1994.
Fishwild, et al., High-avidity human IgG kappa monoclonal antibodies from a novel strain of minilocus transgenic mice. Nat Biotechnol 14, 845-851, 1996.
Neuberger, Generating high-avidity human Mabs in mice. Nat Biotechnol 14, 826, 1996.
Angerer, et al., Demonstration of tissue-specific gene expression by in situ hybridization. Methods Enzymol 152, 649-661, 1987.

Wu, et al., The ligation amplification reaction (LAR)—amplification of specific DNA sequences using sequential rounds of template-dependent ligation. Genomics 4, 560-569, 1989.
Landegren, et al., A Ligase-Mediated Gene Detection Technique. Science 241, 1077-1080, 1988.
Barringer, et al., Blunt-end and single-strand ligations by *Escherichia coli* ligase: influence on an in vitro amplication scheme. Gene 89, 117-122, 1990.
Kwoh, et al., Transcription-based amplification system and detection of amplified human immunodeficiency virus type 1 with a bead-based sandwich hybridization format. Proc Natl Acad Sci USA 86, 1173-1177, 1989.
Gautelli, et al., Isothermal, in vitro amplification of nucleic acids by a multienzyme reaction modeled after retroviral replication. Proc Natl Acad Sci USA 87, 1874-1878, 1990.
Holland, et al., Detection of specific polymerase chain reaction product by utilizing the 5'—3' exonuclease activity of Thermus aquaticus DNA polymerase. Proc Natl Acad Sci 88, 7276-7280, 1991.
Boerner, et al., Production of antigen-specific human monoclonal antibodies from in vitro-primed human splenocytes. J Immunol 147, 86-95, 1991.
Lipinski, et al., Experimental and computational approaches to estimate solubility and permeability in drug discovery and development settings. Adv Drug Deliv Rev 23, 3-25, 1997.
Lo, et al., Updates and future horizons on the understanding, diagnosis, and treatment of Sturge-Weber syndrome brain involvement. Dev Med Child Neural 54, 214-23, 2012.

* cited by examiner

DIAGNOSTIC AND PROGNOSTIC TEST FOR STURGE-WEBER SYNDROME, KLIPPEL-TRENAUNAY-WEBER SYNDROME, AND PORT-WINE STAINS (PWSS)

CROSS-REFERENCE TO RELATED APPLICATIONS

This application is a 35 U.S.C. § 371 U.S. national entry of International Application PCT/US2014/034319 having an international filing date of Apr. 16, 2014, which claims the benefit of U.S. Provisional Application No. 61/812,309, filed Apr. 16, 2013, the content of each of the aforementioned applications is herein incorporated by reference in their entirety.

STATEMENT OF GOVERNMENTAL INTEREST

This invention was made with government support under grant number NS065705 awarded by the National Institutes of Health. The government has certain rights in the invention.

FIELD OF THE INVENTION

The present invention relates to the fields of neurologic, ophthalmologic, orthopedic and skin disorders. More specifically, the present invention provides methods and compositions for diagnosing and prognosing Sturge-Weber Syndrome (SWS), Klippel-Trenaunay-Weber Syndrome (KTWS), and Port Wine Stains (PWS).

INCORPORATION-BY-REFERENCE OF MATERIAL SUBMITTED ELECTRONICALLY

This application contains a sequence listing. It has been submitted electronically via EFS-Web as an ASCII text file entitled "P12119-04_ST25.txt." The sequence listing is 10,275 bytes in size, and was created on Mar. 18, 2016. It is hereby incorporated by reference in its entirety.

BACKGROUND OF THE INVENTION

Sturge-Weber syndrome (SWS), also known as encephalofacial angiomatosis, is a neurocutaneous disorder that occurs as a sporadic, congenital condition characterized by a port-wine stain (PWS) affecting the V1 territory of the face (the forehead and/or eyelid) associated with a leptomengial angioma of the brain and venous abnormalities of the eye. It occurs in both males and females, in approximately 1 in 20-50,000 live births. Independently occurring port-wine stains are much more common, occurring in approximately 3 in 1000 births and commonly involve the head and neck. A child born with a port-wine stain on the face has approximately a 6% chance of having SWS, and this risk increases to 26% when the PWS is located in the V1 territory of the face. Port-wine stains commonly have underlying soft and bony tissue hypertrophy which may be mild or massive. When a port-wine stain-associated hypertrophy involves a limb and has enlarged venous or lymphatic vessels this is referred to as Klippel-Trenaunay Weber syndrome (KTWS). KTWS has been reported in association with SWS when the PWS is extensive and extends down on to the trunk and affected limb. Therefore, it has been hypothesized that SWS, KTWS, and PWS are likely to have the same underlying somatic mutation(s). According to this hypothesis the precise clinical manifestations are dependent upon where and when in the developing fetus the somatic mutation occurs.

SUMMARY OF THE INVENTION

The present invention is based, at least in part, on the discovery of an identifying mosaic somatic mutation in a specific gene that can be used to detect, diagnose and prognose SWS, KTWS, related neurocutaneous disorders and PWS.

Sturge-Weber syndrome (SWS) is a neurocutaneous disorder that occurs as a sporadic, congenital condition. It is characterized by a capillary malformation of the skin, i.e., port-wine stain (PWS) affecting the V1 distribution of the face (forehead and/or eyelid) and abnormal capillary-venous vessels in the leptomeninges of the brain (leptomeningeal angioma), sometimes associated with abnormal venous vessels in the eye and glaucoma. SWS is frequently associated with intractable seizures and intellectual disability. Given its sporadic occurrence and the scattered or asymmetric distribution of vascular malformations, both PWS and SWS are hypothesized to be caused by a mosaic somatic mutation that disrupts normal vascular development.

The present inventors tested this hypothesis by performing whole genome sequencing of DNA from paired visibly affected and normal tissue samples (n=3 SWS subjects). The presence of a somatic mosaic mutation was assayed in 97 samples from 50 SWS, PWS, or control subjects using amplicon sequencing and SNaPshot assays. The effects of the mutation on downstream signaling were queried using phosphorylation-specific antibodies for relevant effectors, and a luciferase reporter assay.

The present inventors identified a non-synonymous single-nucleotide variant (c.548G>A, p.Arg183Gln) in GNAQ in samples of affected tissue from 88% (23/26) of subjects with SWS, 92% (12/13) of apparently non-syndromic PWS, none of the samples affected tissue from four (0/4) subjects with an unrelated cerebrovascular malformation, and no tissues from six (0/6) normal subjects. Mutant allele prevalence in affected tissues ranged from 1% to 18.1%. Extracellular signal-regulated kinase (ERK) activity was modestly increased during trans-expression of mutant GNAQ.

In one embodiment, diagnostic and prognostic detection of a sequence mutation in Gnaq is performed by determining the number of alleles in a biological sample having a sequence mutation in Gnaq. In another embodiment, diagnostic and prognostic detection of a sequence mutation in Gnaq is performed by determining the percentage of wild-type alleles and mutant alleles (having a sequence mutation in Gnaq) in DNA derived from a set of cells. In another specific embodiment, a method for identifying a human patient as having or likely to have Sturge-Weber syndrome (SWS) comprises the steps of (a) providing a nucleic acid sample from the human patient; (b) detecting whether the somatic mutation c.548G>A in the guanine nucleotide-binding protein G subunit alpha (GNAQ) gene is present in the nucleic acid sample; and (c) identifying the human patient as having or likely have SWS when the somatic mutation c.548G>A is present. In a more specific embodiment, whether the mutation comprises an assessment of the number of alleles in the sample comprising the mutation. For example, the assessment can comprise determining the percentage of mutatent alleles in the sample the comprise the mutation.

In certain embodiments, the detecting step is performed using next generation sequencing. In particular embodiments, the detecting step is performed using a single nucleotide primer extension assay, whole genome sequencing, whole exome sequencing or targeted amplicon sequencing. In certain embodiments, a detecting step comprises performing polymerase chain reaction (PCR). In a specific embodiment, the primers listed in SEQ ID NO:1 and SEQ ID NO:2 are used. In other embodiments, the primers further comprise SEQ ID NO:3 and SEQ ID NO:4.

In another aspect, the present invention provides methods for treating SWS. In one embodiment, a method for treating a human patient having SWS comprises the steps of (a) providing a nucleic acid sample from the human patient; (b) detecting whether the somatic mutation c.548G>A in the guanine nucleotide-binding protein G subunit alpha (GNAQ) gene is present in the nucleic acid sample, wherein the detecting step is performed via whole genome sequencing, whole exome sequencing or targeted amplicon sequencing; (c) identifying the human patient as having or likely have SWS when the somatic mutation c.548G>A is present; and (d) administering a GNAQ inhibitor to the human patient. In another embodiment, the method further comprises administering to the human patient an inhibitor of downstream effectors of the GNAQ signaling pathway. In certain embodiments, the inhibitor is a protein kinase C (PKC) inhibitor, a MEK inhibitor, a PI3k/AKT inhibitor, a phospholipase Cβ inhibitor or combinations thereof.

In a further aspect, the present invention provides methods for monitoring treatment of a patient with Sturge-Weber syndrome (SWS). In one embodiment, a method for monitoring treatment of a patient with Sturge-Weber syndrome (SWS) comprises the steps of (a) providing a sample from the patient undergoing treatment; (b) determining the number of alleles in the sample comprising the somatic mutation c.548G>A in the guanine nucleotide-binding protein G subunit alpha (GNAQ) gene or p.R183Q in the GNAQ protein; (c) comparing the number of alleles comprising the somatic mutation to the number of alleles comprising the somatic mutation from a patient sample provided prior to undergoing treatment; and (d) determining that the patient is improving if there is a decrease in the number of alleles comprising the somatic mutation from the sample of step (a). In a further embodiment, the method further comprises adjusting patient treatment based on step (d). In a specific embodiment, the determining step comprises performing a single nucleotide primer extension assay. In a more specific embodiment, the assay is a snapshot assay. In another specific embodiment, the primers used to perform the assay are SEQ ID NO:3 and SEQ ID NO:4.

In another embodiment, a method to monitor progress of SWS treatment in a patient comprises (a) determining in a test sample relative to normal sample, a somatic mutation in the GNAQ gene; (b) repeating one or more times the determining step; and (c) identifying an increase, decrease or stable level of the mutation in the test sample over time. In a more specific embodiment, the somatic mutation in the GNAQ gene is c.548G>A. In a further embodiment a method for monitoring the response of patient with SWS to therapy comprises the steps of (a) administering a therapy to the patient; (b) obtaining a nucleic acid sample from the patient; and (c) determining whether a somatic mutation at c.548G>A of the GNAQ gene is present. In yet another embodiment, a method for monitoring the response of patient with SWS to therapy comprises the steps of (a) administering a therapy to the patient; (b) obtaining a biological sample from the patient; and (c) determining whether a somatic mutation at p.R183Q of the GNAQ protein is present. In certain embodiments, the methods further comprise adjusting treatment of the patient based on step (c).

In another aspect, the present invention provides methods for treating or monitoring treatment of a patient with Klippel-Trenaunay-Weber Syndrome (KTWS). In a specific embodiment, a method for monitoring treatment of a patient with KTWS comprises the steps of (a) providing a sample from the patient undergoing treatment; (b) determining the number of alleles in the sample comprising the somatic mutation c.548G>A in the guanine nucleotide-binding protein G subunit alpha (GNAQ) gene or p.R183Q in the GNAQ protein; (c) comparing the number of alleles comprising the somatic mutation to the number of alleles comprising the somatic mutation from a patient sample provided prior to undergoing treatment; and (d) determining that the patient is improving if there is a decrease in the number of alleles comprising the somatic mutation from the sample of step (a). In a specific embodiment, the determining step comprises performing a single nucleotide primer extension assay. In a further embodiment, the method further comprises adjusting patient treatment based on step (d).

In another embodiment, a method to monitor progress of KTWS treatment in a patient comprises (a) determining in a test sample relative to normal sample, a somatic mutation in the GNAQ gene; (b) repeating one or more times the determining step; and (c) identifying an increase, decrease or stable level of the mutation in the test sample over time. In a more specific embodiment, the somatic mutation in the GNAQ gene is c.548G>A. In a further embodiment, a method for monitoring the response of patient with KTWS to therapy comprises the steps of (a) administering a therapy to the patient; (b) obtaining a nucleic acid sample from the patient; and (c) determining whether a somatic mutation at c.548G>A of the GNAQ gene is present. In a further embodiment, a method for monitoring the response of patient with KTWS to therapy comprises the steps of (a) administering a therapy to the patient; (b) obtaining a biological sample from the patient; and (c) determining whether a somatic mutation at p.R183Q of the GNAQ protein is present.

In a further aspect, the present invention provides methods for treating or monitoring treatment of progress of patient with Port Wine Stains (PWS). In a specific embodiment, a method for monitoring treatment of a patient with Port Wine Stains (PWS) comprises the steps of (a) providing a sample from the patient undergoing treatment; (b) determining the number of alleles in the sample comprising the somatic mutation c.548G>A in the guanine nucleotide-binding protein G subunit alpha (GNAQ) gene or p.R183Q in the GNAQ protein; (c) comparing the number of alleles comprising the somatic mutation to the number of alleles comprising the somatic mutation from a patient sample provided prior to undergoing treatment; and (d) determining that the patient is improving if there is a decrease in the number of alleles comprising the somatic mutation from the sample of step (a). In a further embodiment, the method further comprises adjusting patient treatment based on step (d).

In another embodiment, a method for prognosing or monitoring treatment of a patient with SWS, KTWS and/or PWS comprises the steps of (a) providing a sample from the patient undergoing treatment; (b) determining the number of alleles in the sample comprising at least one activating somatic mutation in the guanine nucleotide-binding protein G subunit alpha (GNAQ) gene or protein; (c) comparing the number of alleles comprising the at least one somatic mutation to the number of alleles comprising the somatic mutation from a patient sample provided prior to undergoing treatment; and (d) determining that the patient is improving if there is a decrease in the number of alleles comprising the at least one somatic mutation from the sample of step (a). In a further embodiment, the method further comprises adjusting patient treatment based on step (d). In another embodiment, the at least one activating somatic mutation in the GNAQ gene or protein is c.548G>A or p.R183Q, respectively.

In another aspect, the present invention provides methods and compositions useful for treating PWS and/or SWS. In certain embodiments, the methods and compositions utilize a GNAQ modulator. In one embodiment, the modulator is an antagonist or inhibitor of GNAQ. In an alternative embodiment, the modulator is an agonist of GNAQ. In specific embodiments, the GNAQ antagonist is a small molecule, an antibody, or an inhibitory nucleic acid molecule (e.g., siRNA, antisense, or shRNA).

DETAILED DESCRIPTION OF THE INVENTION

Figure 1:
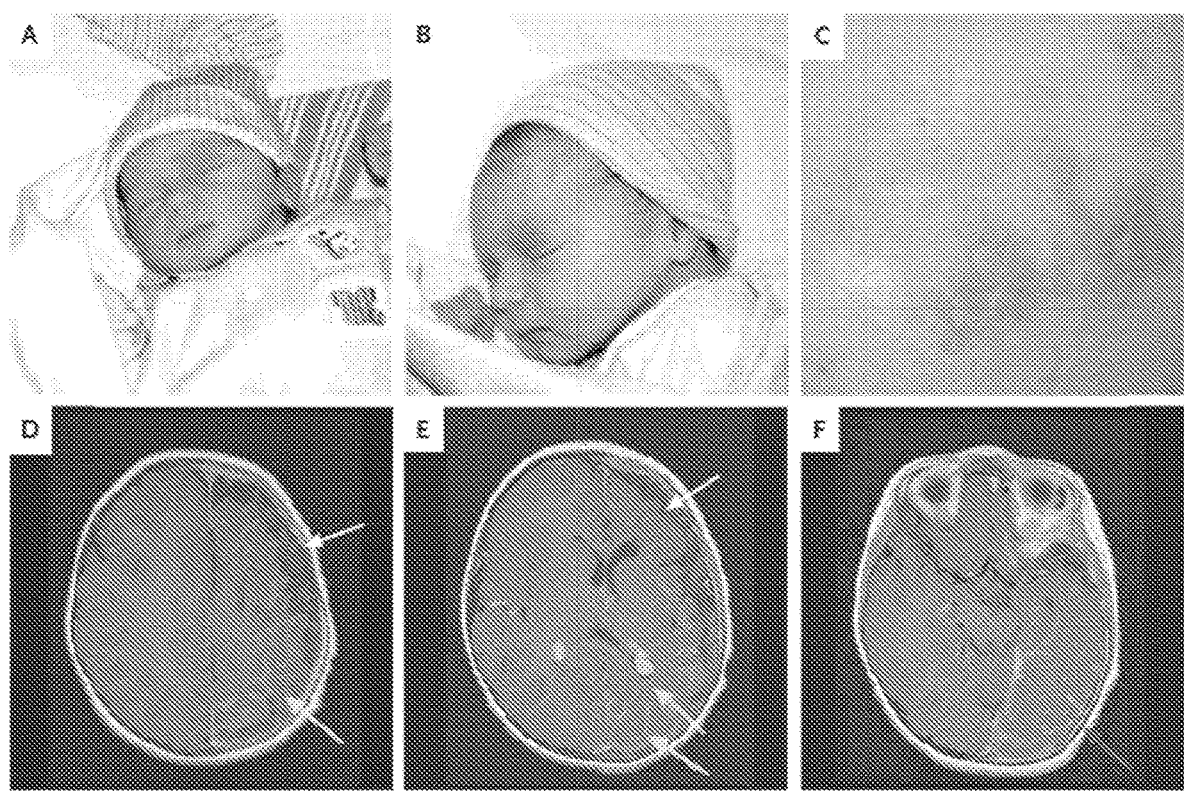
FIG. 1: Photographs and MRI images from representative individuals with Sturge-Weber syndrome or isolated port-wine stain. (A, B) Facial PWS birthmark photographed at birth in subject 37; note the left-sided V1 distribution. Child began having seizures at 7 months of life. (C) Isolated PWS birthmark of the left shoulder from subject 11 (see Table 1); birthmark is flat and red without evidence of hypertrophy or cobble-stoning or any other associated vascular or lymphatic anomaly. (D-F) Axial contrast-enhanced MRI imaging of the brain of a representative individual demonstrating left-sided hemispheric leptomeningeal enhancement (white arrows), an enlarged and enhancing left-sided choroid plexus (red arrow) and left hemispheric brain atrophy (yellow arrows).

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The term "Gnaq" refers to the alpha subunit of a guanine nucleotide binding protein (G-protein). The term encompasses nucleic acid and polypeptide polymorphic variants, alleles, mutants, and fragments of Gnaq. Such sequences are well known in the art.

Exemplary human Gnaq sequences are available under the reference sequences NM_002072 in the NCBI nucleotide database (nucleotide sequence) (and NM_002072.3) and accession number NP 002063.2 (polypeptide sequence). The sequence NM_002072 is provided as SEQ ID NO:12 as an exemplary nucleotide sequence. The exemplary polypeptide sequence is shown in SEQ ID NO:13.

A "Gnaq-dependent mutation" as used in the context of this application refers to cells that have a defect in Gnaq that activates or otherwise disrupts the function of Gnaq, i.e., has an "activating" mutation, in comparison to cells that do not have the mutation, and leads to a loss or decrease of GTP hydrolyzing activity of the mutant G-α subunit. The Gnaq mutation, e.g., a substitution mutation, can result in constitutive activity of the protein. The "Gnaq-dependent mutation" may have one or more of such mutations, e.g., the cells may have somatic substitution mutation involving R183. A "Gnaq-dependent mutation" may also have mutations in genes other than Gnaq.

The terms "sample," "patient sample," "biological sample," and the like, encompass a variety of sample types obtained from a patient, individual, or subject and can be used in a diagnostic, prognostic or monitoring assay. The patient sample may be obtained from a healthy subject, a diseased patient including, for example, a patient having associated symptoms of SWS, KTWS or PWS. Moreover, a sample obtained from a patient can be divided and only a portion may be used for diagnosis, prognosis or monitoring. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a skin sample. In another embodiment, a sample of brain tissue is used. In other embodiments, a sample comprises a blood or serum sample. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The terms "providing a sample" and "providing a biological (or patient) sample" are used interchangeably and mean to provide or obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, can also be used.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm nih gov/BLAST/ or the like). Such sequences are then said to be "substantially identical." This definition also refers to, or may be applied to, the complement of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length. For example, a nucleic acid probe that is used in the invention, may have at least 85%, typically 90%, or 95%, sequence identity to a contiguous region of SEQ ID NO:12.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local alignment algorithm of Smith & Waterman, Adv. Appl. Math. 2:482 (1981), by the alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Examples of algorithms that are suitable for determining percent sequence identity and sequence similarity include the BLAST and BLAST 2.0 algorithms, which are described in Altschul et al., Nuc. Acids Res. 25:3389-3402 (1977) and Altschul et al., J. Mol. Biol. 215:403-410 (1990). For the purposes of this invention, BLAST and BLAST 2.0 are used with default parameters to determine percent sequence identity for the nucleic acids and proteins of the invention. Software for performing BLAST analyses is publicly available through the National Center for Biotechnology Information (NCBI). The BLASTN program (for nucleotide sequences) uses as defaults a wordlength (W) of 11, an expectation (E) of 10, a cutoff of 100, match score=2, mismatch score=−3, and a comparison of both strands. For amino acid (protein) sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915)). For the purposes of this invention, the BLAST2.0 algorithm is used with the default parameters and the filter off.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. In certain embodiments, it means that the nucleic acid or protein is at least 85% pure, at least 95% pure, and at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, e.g., an .alpha. carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of ordinary skill in the art recognizes that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typical conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the KIT nucleic acids, proteins and antibodies at any position. Any method known in the art for conjugating the antibody to the label may be employed, e.g., using methods described in Hermanson, Bioconjugate Techniques 1996, Academic Press, Inc., San Diego.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. Similarly, a "recombinant protein" is a protein made using recombinant techniques, i.e., through the expression of a recombinant nucleic acid as depicted above.

The phrase "selectively (or specifically) hybridizes to" refers to the binding, duplexing, or hybridizing of a molecule to a particular nucleotide sequence under stringent hybridization conditions when that sequence is present in a mixture (e.g., total cellular or library DNA or RNA, an amplification reaction), such that the binding of the molecule to the particular nucleotide sequence is determinative of the presence of the nucleotide sequence is the mixture.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec. to 2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The phrase "functional effects" in the context of assays for testing compounds that inhibit activity of a Gnaq protein includes the determination of a parameter that is indirectly or directly under the influence of the Gnaq protein or nucleic acid, e.g., a functional, physical, or chemical effect, such as the ability to alter GTP hydrolase activity. Activities or functional effect of Gnaq can include protein-protein interaction activity, e.g., the ability of Gnaq to bind an antibody or other protein with which it interacts; GTP hydrolase activity, the ability of Gnaq to bind GTP and/or GDP; contact inhibition and density limitation of growth; cellular proliferation; cellular transformation; changes in pigmentation; growth factor or serum dependence; and mRNA and protein expression in cells. "Functional effects" include in vitro, in vivo, and ex vivo activities.

As used herein, "inhibitors" or "antagonists" of Gnaq (e.g. "Gnaq antagonists") refer to modulatory molecules or compounds that, e.g., bind to, partially or totally block activity, decrease, prevent, delay activation, inactivate, desensitize, or down regulate the activity or expression of Gnaq protein, phospholipase Cβ, or downstream molecules regulated by Gnaq, e.g., protein kinase C (PKC). In a specific embodiment, an inhibitor specifically inhibits the mutant Gnaq described herein. In such embodiments, exogenous wild-type Gnaq can be administered in conjunction with the specific Gnaq inhibitor. Inhibitors can include siRNA or antisense RNA, genetically modified versions of Gnaq protein, e.g., versions with altered activity, as well as naturally occurring and synthetic Gnaq antagonists, antibodies, small chemical molecules and the like. Gnaq inhibitors for use in the invention are known in the art. For example, non-limiting exemplary inhibitors suitable for use with the present invention can include inhibitors of PKC, for example the relatively nonspecific PKC inhibitor staurosporine, the staurosporie analogue CPG41251, bryostatin-1, KAI-9803, 7-hydroxystaurosporine, L-threo-dihydrosphingosine (safingol), the non-selective PKC inhibitor (PKC412), ilmofosine (BM 41 440), indolcarbazole Go6796 which is a more specific inhibitor of the classical PKC isoforms including PKC.mu., the PKC-alpha antisense inhibitor LY900003, and the PKC-beta inhibitors LY333531, LY317615 (Enzastaurin). Non-limiting exemplary inhibitors of phospholipase C3 can include edelfosine and fluvirusin B[2]. Assays for identifying other inhibitors can be performed in vitro or in vivo, e.g., in cells, or cell membranes, by applying test inhibitor compounds, and then determining the functional effects on activity.

In some embodiments, samples or assays comprising Gnaq proteins that are treated with a potential inhibitor are compared to control samples without the inhibitor, to examine the effect on activity. Typically, control samples, e.g., cells, that have a Gnaq mutation and that are untreated with inhibitors are assigned a relative protein activity value of 100%. Inhibition of Gnaq is achieved when the activity value relative to the control is changed at least about 20%, at least about 50%, at least about 75-100%, or more. In some embodiments, an inhibitor will activate a particular activity, such as GTP hydrolysis, however, the net effect will be a decrease in the activity of Gnaq, e.g., in comparison to controls that have activated Gnaq.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab').sub.2, Fab, Fv and rIgG. See also, Pierce Catalog and Handbook, 1994-1995 (Pierce Chemical Co., Rockford, Ill.). See also, e.g., Kuby, J., Immunology, 3.sup.rd Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

An antibody immunologically reactive with a particular antigen can be generated by recombinant methods such as selection of libraries of recombinant antibodies in phage or similar vectors, see, e.g., Huse et al., Science 246:1275-1281 (1989); Ward et al., Nature 341:544-546 (1989); and Vaughan et al., Nature Biotech. 14:309-314 (1996), or by immunizing an animal with the antigen or with DNA encoding the antigen.

Typically, an immunoglobulin has a heavy and light chain Each heavy and light chain contains a constant region and a variable region, (the regions are also known as "domains"). Light and heavy chain variable regions contain four framework" regions interrupted by three hypervariable regions, also called complementarity-determining regions (CDRs).

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The term "fully human antibody" refers to an immunoglobulin comprising human hypervariable regions in addition to human framework and constant regions. Such antibodies can be produced using various techniques known in the art. For example in vitro methods involve use of recombinant libraries of human antibody fragments displayed on bacteriophage (e.g., McCafferty et al., 1990, Nature 348: 552-554; Hoogenboom & Winter, J. Mol. Biol. 227:381 (1991); and Marks et al., J. Mol. Biol. 222:581 (1991)), yeast cells (Boder and Wittrup, 1997, Nat Biotechnol 15:553-557), or ribosomes (Hanes and Pluckthun, 1997, Proc Natl Acad Sci USA 94:4937-4942). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584; 5,545,807; 5,545,806; 5,569,825; 5,625, 126; 5,633,425; 5,661,016, and in the following scientific publications: (e.g., Jakobavits, Adv Drug Dehv Rev. 31:33-42 (1998), Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance See, e.g., Epitope Mapping Protocols in Methods in Molecular Biology, Vol. 66, Glenn E. Morris, Ed (1996).

II. GNAQ Mutations

In one aspect of the invention, the presence of an activating mutation in a Gnaq polynucleotide, e.g., mRNA or genomic DNA, or increased activity of a Gnaq protein and/or the presence of a sequence mutation in the Gnaq protein, is determined in biological samples. In some embodiments activating mutations in Gnaq nucleic acids are determined. As noted, human Gnaq sequences are well known. The Gnaq gene maps to 9q21 and the mRNA transcript is 2.188 kb, which encodes a 359 amino acid protein.

"Sequence mutation" as used herein refers to changes in a polynucleotide sequence that result in changes to protein activity. Mutations can be nucleotide substitutions, such as single nucleotide substitutions, insertions, or deletions. Gnaq mutations are typically activating mutations that lead to constitutive activation of Gnaq activity. Without being bound to a theory, it is believed that the constitutive activity results from a lack of the GTP-hydrolase activity in the mutant Gnaq protein.

The present invention is based in part on the discovery of heterozygous somatic activating mutations present in Gnaq in patients with SWS, KTWS and PWS. A mutation may be in any part of the Gnaq gene where the mutation leads to activation of Gnaq. In one embodiment, the mutation 547C>T results in an amino acid substitution, R183Q.

In the present invention, an altered level of Gnaq activity and/or a sequence mutation in Gnaq is detected for the diagnosis, prognosis or treatment monitoring of patients with SWS, KTWS, or PWS. Thus, biological samples obtained from patients that have SWS, KTWS and/or PWS can be analyzed for mutations in the sequence of Gnaq DNA, mRNA or protein. The presence of a mutation is conveniently analyzed using samples of RNA, DNA, or protein.

1. Detection of GNAQ Sequence Mutations

In one embodiment, diagnostic and prognostic detection of a sequence mutation in Gnaq is performed by determining the number of alleles in a biological sample having a sequence mutation in Gnaq. In another embodiment, diagnostic and prognostic detection of a sequence mutation in Gnaq is performed by determining the percentage of wild-type alleles and mutant alleles (having a sequence mutation in Gnaq) in DNA derived from a set of cells. Methods of evaluating the sequence of a particular gene are well known to those of skill in the art, and include, inter alia, hybridization and amplification based assays. In a specific embodiment, sequence mutation in Gnaq can be determined using a probe that selectively hybridizes to the mutant sequence. In other embodiments, sequencing can be used to identify the Gnaq mutation in cells.

In some embodiments, a Gnaq sequence mutation in a biological sample is determined by in situ hybridization, e.g., fluorescence in situ hybridization. In situ hybridization assays are well known (e.g., Angerer (1987) Meth. Enzymol 152: 649). The probes used in such applications specifically hybridize to the region of the Gnaq sequence harboring the mutation. Probes are sufficiently long, e.g., from about 10, 15, or 20 nucleotides to about 50 or more nucleotides, so as to specifically hybridize with the target nucleic acid(s) under stringent conditions.

Any of a number of other hybridization-based assays can be used to detect a sequence mutation in Gnaq in the cells of a biological sample. For example, dot blots, array-based assays and the like can be used to determine Gnaq sequence mutations.

In some embodiments, amplification-based assays are used to detect sequence mutations in Gnaq or to measure the levels of Gnaq transcript. In such an assay, the Gnaq nucleic acid sequence acts as a template in an amplification reaction (e.g., Polymerase Chain Reaction, or PCR). Exemplary amplification-based assays can include RT-PCR methods well known to the skilled artisan (see, e.g., Ausubel et al., supra). Detailed protocols for PCR of DNA and RNA, including quantitative amplification methods, are known (see, e.g., Innis et al. (1990) PCR Protocols, A Guide to Methods and Applications, Academic Press, Inc. N.Y.; and Ausubel and Russell & Sambrook, both supra). The known nucleic acid sequences for Gnaq (see, e.g., SEQ ID NO:12) are sufficient to enable one of skill to routinely select primers to amplify any portion of the gene. Suitable primers for amplification of specific sequences can be designed using principles well known in the art (see, e.g., Dieffenfach & Dveksler, PCR Primer: A Laboratory Manual (1995)).

Other suitable amplification methods include, but are not limited to, ligase chain reaction (LCR) (see, Wu and Wallace (1989) Genomics 4: 560, Landegren et al. (1988) Science 241:1077, and Barringer et al. (1990) Gene 89: 117), transcription amplification (Kwoh et al. (1989) Proc. Natl. Acad. Sci. USA 86: 1173), self-sustained sequence replication (Guatelli et al. (1990) Proc. Nat. Acad. Sci. USA 87: 1874), dot PCR, and linker adapter PCR, etc.

The presence of mutations in Gnaq DNA or RNA sequences can be determined using any technique known in the art. For example, in one embodiment, allele-specific oligonucleotide hybridization may be used, which relies on distinguishing a mutant from a normal nucleic acid sequence using an oligonucleotide that specifically hybridizes to the mutant or normal nucleic acid sequence. This method typically employs short oligonucleotides, e.g., 15-20 nucleotides, in length, that are designed to differentially hybridize to the normal or mutant allele. Guidance for designing such probes is available in the art. The presence of a mutant allele is determined by measuring the amount of allele-specific oligonucleotide that hybridizes to the sample Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099.

In other embodiments, the presence (or amount) of a normal or mutant Gnaq nucleic acid can be detected using allele-specific amplification or primer extension methods. These reactions typically involve use of primers that are designed to specifically target a normal or mutant allele via a mismatch at the 3' end of a primer. The presence of a mismatch affects the ability of a polymerase to extend a primer when the polymerase lacks error-correcting activity. The amount of amplified product can be determined using a probe or by directly measuring the amount of DNA present in the reaction.

Detection of levels of Gnaq nucleic acids, e.g., levels of normal and/or mutant Gnaq polynucleotides, or the presence of a Gnaq mutation can also be performed using a quantitative assay such as a 5'-nuclease activity (also referred to as a "TaqMan®" assay), e.g., as described in U.S. Pat. Nos. 5,210,015; 5,487,972; and 5,804,375; and Holland et al., 1988, Proc. Natl. Acad. Sci. USA 88:7276-7280. In such an assay, labeled detection probes that hybridize within the amplified region are added during the amplification reaction. In some embodiments, the hybridization probe can be an allele-specific probe that discriminates a normal or mutant allele. Alternatively, the method can be performed using an allele-specific primer and a labeled probe that binds to amplified product. In other embodiments, the probe may not discriminate between a mutant and normal allele.

In other embodiments, the presence of a mutant Gnaq allele can be conveniently determined using conventional or next-generation DNA sequencing, such as pyrosequencing, or other known sequencing techniques. Other detection methods include single-stranded conformational polymorphism or restriction fragment length polymorphism detection methods and denaturing gradient gel electrophoresis analysis.

As indicated above, in some embodiments, levels of Gnaq RNA are detected. Methods of detecting and/or quantifying the level of Gnaq gene transcripts (mRNA or cDNA made therefrom) using nucleic acid hybridization techniques are known to those of skill in the art. For example, expression levels of Gnaq can also be analyzed by techniques such as RT-PCR, e.g., using real-time RT-PCR using allele-specific primers or probes, dot blotting, in situ hybridization, RNase protection, probing DNA microchip arrays, and the like.

Overexpression of Gnaq, either mutated sequences or normal nucleic acid and/or polypeptide sequences, can be detected, e.g., using quantitative sequences known in the art such as those described herein. Overexpression is determined with reference to a control, e.g., a normal tissue.

2. Detection of GNAQ Protein or Activity

Altered Gnaq expression and/or activity can also be detected by detecting Gnaq protein or activity. For example, detection of Gnaq protein activity or the presence of Gnaq proteins that have a mutation, can be used for diagnostic, prognostic or treatment monitoring purposes or in screening assays. In some embodiments, the level of Gnaq or the presence of a normal or mutant Gnaq polypeptide in a sample is conveniently determined using immunological assays. In other embodiments, Gnaq activity can be used to determine the presence of activating mutation of Gnaq in a biological sample.

Antibodies can be used to detect Gnaq or can be assessed in the methods of the invention for the ability to inhibit Gnaq. The detection and/or quantification of Gnaq can be accomplished using any of a number of well recognized immunological binding assays. A general overview of the applicable technology can be found in Harlow & Lane, Antibodies: A Laboratory Manual (1988) and Harlow & Lane, Using Antibodies (1999). Other resources include see also Methods in Cell Biology: Antibodies in Cell Biology, volume 37 (Asai, ed. 1993); Basic and Clinical Immunology (Stites & Ten, eds., 7th ed. 1991, and Current Protocols in Immunology (Coligan, et al. Eds, John C. Wiley, 1999-present) Immunological binding assays can use either polyclonal or monoclonal antibodies. In some embodiments, antibodies that specifically detect mutant Gnaq molecules are employed.

Commonly used assays include noncompetitive assays (e.g., sandwich assays) and competitive assays. In competitive assays, the amount of Gnaq present in the sample is measured indirectly by measuring the amount of a known, added (exogenous) Gnaq displaced (competed away) from an anti-Gnaq antibody by the unknown Gnaq present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers, which are then detected according to standard techniques (see Monroe et al., Amer. Clin. Prod. Rev. 5:34-41 (1986)).

Immunoassays also often use a labeling agent to specifically bind to and label the complex formed by the antibody and antigen. The labeling agent may itself be one of the moieties comprising the antibody/antigen complex. Thus, the labeling agent may be a labeled Gnaq polypeptide or a labeled anti-Gnaq antibody. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. The labeling agent can be modified with a detectable moiety, such as biotin, to which another molecule can specifically bind, such as streptavidin. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent compounds (e.g., fluorescein isothiocyanate, Texas red, rhodamine, fluorescein, and the like), radiolabels, enzymes (e.g., horse radish peroxidase, alkaline phosphatase and others commonly used in an ELISA), streptavidin/biotin, and colorimetric labels such as colloidal gold or colored glass or plastic beads (e.g., polystyrene, polypropylene, latex, etc.). Chemiluminescent compounds may also be used. For a review of various labeling or signal producing systems that may be used, see U.S. Pat. No. 4,391,904.

Antibodies to Gnaq are commercially available (e.g., Genesis Biotech, Inc. Taipei County, Taiwan). In some embodiments, mutations to Gnaq can be detected using antibodies that specifically bind a mutant form, thus immunoassays can also be used to detect mutant Gnaq proteins.

Gnaq or a fragment thereof, e.g., the portion of the peptide frequently comprising a sequence mutation, may be used to produce antibodies specifically reactive with Gnaq. For example, a recombinant Gnaq or an antigenic fragment thereof, is isolated. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then used to generate antibodies.

Methods of producing polyclonal and monoclonal antibodies that react specifically with Gnaq are known to those of skill in the art (see, e.g., Coligan; Harlow & Lane, both supra). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)). Such antibodies can be used for diagnostic or prognostic applications, e.g., in the detection of mutated Gnaq.

Typically, polyclonal antisera with a titer of $10^4$ or greater are selected and tested for cross reactivity against non-Gnaq proteins or even other related proteins from other organisms, using a competitive binding immunoassay. Specific polyclonal antisera and monoclonal antibodies will usually bind with a Kd of at least about 0.1 mM, more usually at least about 1 µM, optionally at least about 0.1 µM or better, and optionally 0.01 µM or better.

In some embodiments, a Gnaq antibody may be used for therapeutic applications. For example, in some embodiments, such an antibody may be used to reduce or eliminate a biological function of Gnaq. That is, the addition of anti-Gnaq antibodies (either polyclonal or preferably monoclonal) to a patient with SWS, KTWS or PWS (i.e., a cell population comprising the Gnaq mutation) may reduce or eliminate the condition.

In certain embodiments, the antibodies to the Gnaq proteins for therapeutic applications are humanized antibodies (e.g., Xenerex Biosciences, Mederex, Inc., Abgenix, Inc., Protein Design Labs, Inc.). Human antibodies can also be produced using various techniques known in the art, including phage display libraries (Hoogenboom & Winter, J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

As appreciated by one of ordinary skill in the art, Gnaq activity can be detected to evaluate expression levels or for identifying inhibitors of activity. The activity can be assessed using a variety of in vitro and in vivo assays, including GTP and GDP binding activity, GTP-hydrolase activity, or measurement of phospholipase cp. In some embodiments Gnaq activity can be evaluated using additional endpoints, such as those associated with transformation or pigmentation. Such assays are described in greater detail in the examples and section detailing methods of identifying additional Gnaq inhibitors. Typically Gnaq activity is determined by measuring the ability to bind a protein to which it interacts, e.g., an antibody, ligand, or other protein, such as signaling molecules.

III. Disease Diagnosis/Prognosis/Monitoring

Gnaq nucleic acid and polypeptide sequences can be used for diagnosis, prognosis and/or treatment monitoring of SWS, KTWS or PWS in a patient. For example, as described above, the sequence, level, or activity of Gnaq in a sample from a patient can be determined, wherein an alteration, e.g., a decrease in the level of expression or activity of Gnaq or a sequence mutation in Gnaq, indicates a reduction in the severity of the condition.

The methods of the present invention can be used to determine the optimal course of treatment in a patient with SWS, KTWS, or PWS. For example, the presence of a sequence mutation in Gnaq can indicate that certain therapeutics, such as those that target Gnaq, phospholipase Cβ, or downstream pathways regulated by Gnaq will be beneficial to those patients. Upstream pathways are also relevant, for example, receptors coupled directly to Gnaq protein. In addition, a correlation can be readily established between the presence of a defect or sequence mutation in Gnaq, and the relative efficacy of one or another anti-SWS, KTWS or PWS agent. Such analyses can be performed, e.g., retrospectively, i.e., by analyzing for a Gnaq defect or sequence mutation in samples taken previously from patients that have subsequently undergone one or more types of therapy, e.g., therapies that target G-proteins or phospholipase Cβ, or other downstream pathways regulated by Gnaq and correlating the presence of the defect with the known efficacy of the treatment.

Often, such methods will be used in conjunction with additional diagnostic methods. In other embodiments, a tissue sample known to contain cells harboring the mutation can be analyzed for Gnaq defects to determine information about the condition, e.g., the efficacy of certain treatments, such as therapeutics that target Gnaq, or downstream pathways regulated by Gnaq.

In some embodiments, the analysis of cells/alleles for the presence of Gnaq defects or sequence mutation can be used to determine the prognosis of a patient with SWS, KTWS, or PWS or for determining progression of the condition. A "diagnostic presence" can be increased levels of Gnaq mRNA or protein and/or activity, and/or the presence of sequence mutations in Gnaq that alter function.

Any biological sample suspected of comprising cells comprising the mutation can be evaluated to determine progression. For example, tissues from visceral organs, blood, lymph nodes and the like can be analyzed for the presence of Gnaq sequence mutations and or increased levels of Gnaq activity.

IV. GNAQ Inhibitors or Modulators and Screening Methods Therefor

In another aspect, the present invention includes methods of treating patients who have a mutation in Gnaq where the method comprises administering an inhibitor or Gnaq antagonist. Inhibitors and Gnaq antagonists are known. For example, non-limiting exemplary inhibitors suitable for use with the present invention can include specific and nonspecific inhibitors of PKC and various PKC isoforms including PKCμ. and PKCε. Exemplary non-limiting inhibitors suitable for use with the present invention include staurosporine, the staurosporine analogue CPG41251, bryostatin-1, KAI-9803, 7-hydroxystaurosporine, L-threo-dihydrosphingosine (safingol), the non-selective PKC inhibitor (PKC412), ilmofosine (BM 41 440), Go6976, which is an indolcarbazole that more specifically inhibits the classical isoforms of PKC, including PCKμ, the PKC-alpha antisense inhibitor LY900003, and the PKC-beta inhibitors LY333531, LY317615 (Enzastaurin). Non-limiting exemplary inhibitors of phospholipase Cβ can include edelfosine and fluvirusin B[2], which are also suitable for use in the present invention.

Other inhibitors include inhibitors such as antibodies, peptide, nucleic acids and the like. As used herein, a Gnaq inhibitor can be a molecule that modulates Gnaq nucleic acid expression and/or Gnaq protein activity, or downstream pathways regulated by Gnaq.

Method of screening for modulators of compounds can employ, for example, cells in which Gnaq is over-expressed or mutated. Such modulators may be candidate Gnaq GTP hydrolase modulators. Additional Gnaq inhibitors can be identified by assaying for Gnaq activity, e.g., GTP binding or GTP hydrolase activity. Such assays employ known Gnaq sequences or fragments, e.g., the guanine binding domain of Gnaq, or variants thereof. An exemplary human Gnaq polypeptide sequence that could be used in such assays is provided in SEQ ID NO:13.

Activity assays are used to identify inhibitors that can be used as therapeutic agents, e.g., antibodies to Gnaq and antagonists of Gnaq activity Inhibitors of Gnaq activity are tested using Gnaq polypeptides, either recombinant or naturally occurring. The protein can be isolated, expressed in a cell, expressed in tissue or in an animal, either recombinant or naturally occurring. For example, transformed cells can be used. Modulation is tested using one of the in vitro or in vivo assays described herein. Activity can also be examined in vitro with soluble or solid state reactions, using a Gnaq fragment that binds to another protein, e.g., phospholipase Cβ, or GTP.

In another embodiment, mRNA and/or protein expression levels can be measured to assess the effects of a test compound on Gnaq expression levels. A host cell expressing Gnaq is contacted with a test compound for a sufficient time to effect any interactions, and then the level of mRNA or protein is measured. The amount of time to effect such interactions may be empirically determined, such as by running a time course and measuring the level of expression as a function of time. The amount of expression may be measured by using any method known to those of skill in the art to be suitable.

The amount of expression is then compared to the amount of expression in the absence of the test compound. A substantially identical cell may be derived from the same cells from which the recombinant cell was prepared but which had not been modified by introduction of heterologous DNA. A difference in the amount of expression indicates that the test compound has in some manner altered Gnaq levels.

In some assays to identify Gnaq inhibitors, samples that are treated with a potential inhibitor are compared to control samples to determine the extent of modulation. Control samples without the mutation and untreated with candidate inhibitors are assigned a relative activity value of 100 Inhibition of Gnaq is achieved when the activity value relative to the control is about 80%, about 50%, or about 25-0%.

The compounds tested as inhibitors of Gnaq can be any small chemical compound, or a biological entity, e.g., a macromolecule such as a protein, sugar, nucleic acid or lipid. Alternatively, modulators can be genetically altered versions of Gnaq. Typically, test compounds will be small chemical molecules and peptides or antibodies.

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a Log P over 5 (or M Log P over 4.15); and/or having more than 10 H-bond acceptors (expressed as the sum of Ns and Os). See, e.g., Lipinski et al. Adv Drug Delivery Res 23:3-25 (1997). Compound classes that are substrates for biological transporters are typically exceptions to the rule.

Essentially any chemical compound can be used as a potential modulator or ligand in the assays of the invention. Most often, compounds can be dissolved in aqueous or organic (especially DMSO-based) solutions. The assays are designed to screen large chemical libraries by automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

Certain screening methods involve screening for a compound that modulates the expression of Gnaq. Such methods generally involve conducting cell-based assays in which test compounds are contacted with one or more cells expressing Gnaq and then detecting a decrease in expression (either transcript or translation product).

Expression can be detected in a number of different ways. As described herein, the expression levels of the protein in a cell can be determined by probing the mRNA expressed in a cell with a probe that specifically hybridizes with a Gnaq transcript (or complementary nucleic acid derived therefrom). Alternatively, protein can be detected using immunological methods in which a cell lysate is probed with antibodies that specifically bind to the protein.

Other cell-based assays are reporter assays conducted with cells that do not express the protein. Often, these assays are conducted with a heterologous nucleic acid construct that includes a promoter that is operably linked to a reporter gene that encodes a detectable product.

V. Treatment And Administration Of Pharmaceutical Compositions

Inhibitors of Gnaq can be administered to a patient for the treatment of SWS, KTWS or PWS having a sequence mutation in Gnaq. As described in detail below, the inhibitors are administered in any suitable manner, optionally with pharmaceutically acceptable carriers. In some embodiments, inhibitors of PKC or phospholipase Cβ are administered. Protocols for the administration of inhibitors are known and can be further optimized for SWS, KTWS or PWS patients based on principles known in the pharmacological arts (Remington's Pharmaceutical Sciences, 17th ed., 1989).

The inhibitors can be administered to a patient at therapeutically effective doses to prevent, treat, or control the condition. The compounds are administered to a patient in an amount sufficient to elicit an effective protective or therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular Gnaq inhibitor employed and the condition of the subject, as well as the body weight or surface area of the area to be treated. The size of the dose also will be determined by the existence, nature, and extent of any adverse effects that accompany the administration of a particular compound in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

V. Kits

The invention also provides kits for diagnostic, prognostic or therapeutic applications. For diagnostic/prognostic applications, such kits may include any or all of the following: assay reagents, buffers, Gnaq probes, primers, antibodies, or the like.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Informed Consent. All studies were performed with approval of the Johns Hopkins or Duke University Institutional Review Board. De-identified samples were obtained with informed consent from subjects with SWS or from the NICHD Maryland Brain and Tissue Bank for Developmental Disorders (MBTBDD). Age, sex, ethnicity and syndrome status (apparently non-syndromic PWS or SWS) were confirmed and recorded from the source along with information regarding surgery, autopsy or procedure providing the tissue.

Whole Genome Sequencing. Genomic DNA was purified from affected or unaffected blood or tissue from three individuals (n=6) using a Qiagen Puregene (blood samples) or DNAeasy (skin and brain) extraction kit and quantitated using a SybrGreen assay. Whole genome sequencing was performed on an Illumina HiSeq 2000 at Illumina, Inc. (San Diego, Calif.) to 33.3× to 50.8× mean depth of coverage. Paired end reads were aligned to the hg19 human reference using the Illumina Genome Analyzer Pipeline. Somatic single nucleotide variants (SNV) or insertion/deletions (indel) were detected using Strelka. Post-call filtration was applied using the author's recommended parameters to remove spurious SNVs and indels resulting from homopolymer repeats and abnormally high read depth regions. Somatic SNV calls from Strelka (from autosomes as well as X chromosome) to the affected samples were identified, and mutant allele frequencies were calculated for each affected/normal pair of WGS. These were identified as potential somatic SNVs. There SNV cells and ranked in order of predicted functional effect using VAAST. 1000 Genomes variants were specified as background to remove variants found in a normal population, and RefSeq genes were used as regions of interest.

Targeted Amplicon Re-Sequencing. An amplicon consisting of 168 bp from GNAQ exon 4 and adjacent intronic sequence (NC_000009.11 80,412,463-80,412,630), encompassing the GNAQ c.548G residue (NC_002072.3), was PCR amplified in a two-stage reaction. For each sample a unique DNA barcode, sequencing adapters, and Illumina flow-cell clustering adapters were added. Barcode sequences were generated using a 7 nucleotide Hamming encoding scheme, allowing for correction of a single base miscall. Paired end sequencing of barcoded amplicons was performed using an Illumina MiSeq, producing 151 nt paired end reads. Reads were aligned to the hg1 human reference using BWA 0.6.2 with base quality trimming Q30. Samtools mpileup of base calls greater than Q30 was used to determine allele counts at the mutation site. Bpipe pipelines not shown. Aligned exome reads from the 1000 Genomes Project {Consortium:2011gj} (alignment release 2011 Nov. 14) were evaluated at the c.548 position for base calls supporting the c.548G>A mutation. Only exomes having a read depth of greater than 100 at the variant site were evaluated. Samples from both amplicon sequencing and 1000 Genomes Project exomes were determined to have a mutation if the percent of reads supporting a mutation exceeded 10 times (1%) the expected base miscall rate (0.1%). The median read depth for amplicon sequencing was selected on the basis of 1,000,000 simulations of a random draw from an allele pool with 1% mutant allele frequency.

Plasmids. Full length wild type GNAQ plasmid was purchased from Origene (Rockville, Md.). This TruORF Gold clone contains the entire reading frame plus Myc and flag epitope tags at the carboxyl terminus Specific mutations, c.548G>A, p.Arg183Gln, and 626A>T, p.Gln209Leu, were introduced into the clone using primers for site directed mutagenesis. Clones were sequenced to verify that no other changes were present. pSRE (serum response element)-Luc (Agilent Technologies) and pSV40-RL (Roche) were used as reporter plasmids for the luciferase assay.

Luciferase Assay. GNAQ-WT, -R183Q, or -Q209L, pSRE-Luc and pSV40-RL at a ratio of 5:200:1 ng were transfected into 293T cells using Fugene 6 (Promega). Cells were lysed after 20-24 hours incubation and the luciferase activity was measured using the Dual-Luciferase Reporter Assay System (Promega) on a Polarstar Optima plate reader (BMG Labtech, Germany). Experiments were performed in triplicate.

SNaPshot Assay. DNA was extracted from archived, formalin-fixed, paraffin-embedded port-wine stain tissue samples according to the manufacturer's protocol (Gentra PureGene, Qiagen). Primers for exon 4 (Table 1) were used to amplify genomic DNA from each of the samples and electrophoresed on a 1% agarose gel. PCR products were extracted using GeneClean Turbo (MP Bio). Purified PCR products were interrogated for their sequence at position c.548 using the SNaPshot Multiplex Kit (Life Technologies, Grand Island, N.Y.) and analyzed on an ABI Prism 3130. Reference and mutant allele frequencies were calculated based on the area of the resulting peaks.

TABLE 1

SNaPshot Primer Sequences

| GNAQ exon 4 amplicon | | Primer sequence |
|---|---|---|
| Forward | 5' | ATTGTGTCTTCCCTCCTCTA (SEQ ID NO: 1) |
| Reverse | 5' | GGTTTCATGGACTCAGTTAC (SEQ ID NO: 2) |
| SNaPshot Forward | 5' | CGCAACAAGATGTGCTTAGAGTTC (SEQ ID NO: 3) |
| SNaPshot Reverse | 5' | TCCCTGTGGTGGGGACT (SEQ ID NO: 4) |

GNAQ exon 4 amplicon forward and reverse primers produce a 207 bp amplicon comprising the sequence of interest. Primers for single base pair extension (SNaPshot) are designed immediately upstream and downstream of the base of interest, c.548G > A.

TABLE 2

SNaPshot Primer Sequences.

| GNA11 exon 4 amplicon | | Primer sequence |
|---|---|---|
| Forward | 5' | GAGCACCCACCGCTGTGTTG (SEQ ID NO: 5) |
| Reverse | 5' | GGCAAATGAGCCTCTCAGTGC (SEQ ID NO: 6) |
| SNaPshot Forward 1 (547C > T) | 5' | CAGGACGTGCTGCGGGTC (SEQ ID NO: 7) |
| SNaPshot Reverse 1 (547C > T) | 5' | TGCCGGTGGTGGGCACGC (SEQ ID NO: 8) |
| SNaPshot Forward 2 (546C > T) | 5' | GCAGGACGTGCTGCGGGT (SEQ ID NO: 9) |
| SNaPshot Forward 3 (548G > A) | 5' | AGGACGTGCTGCGGGTCC (SEQ ID NO: 10) |

TABLE 2-continued

SNaPshot Primer Sequences.

| GNA11 exon 4 amplicon | | Primer sequence |
|---|---|---|
| SnaPshot Reverse 3 (548G > A) | 5' | ATGCCGGTGGTGGGCACG (SEQ ID NO: 11) |

GNA11 exon 4 amplicon forward and reverse primers produce a 207 bp amplicon comprising the sequences of interest. Primers for single base pair extension (SNaPshot) are designed immediately upstream and downstream of the bases of interest, c.547C > T, c.546C > T, and c.548G > A.

Cell Culture and Western Blotting. Human embryonic kidney HEK293T (293T) cells (ATCC, Manassas, Va.) were maintained in Dulbecco's Modified Eagle's Medium (DMEM, Gibco) containing 10% fetal bovine serum at 37° C. in 5% $CO_2$. Cells were grown on 100 $mm^2$ plates and transfected with 6 μg plasmid DNA using FuGene 6 reagent (Roche, Indianapolis, Ind.) according to the manufacturer's protocol. Cell lysates were analyzed by western blotting using standard methods. Antibodies recognizing p44/42 MAPK (Erk1/2) (#9102), Phospho-p44/42 MAPK (Erk1/2) (Thr202/Tyr204, #9101), p38 MAPK (#9212), Phospho-p38 MAPK (Thr180/Tyr182, #9211), Akt (#9272), Phospho-Akt (Ser473, #4058), MARCKS (#5607), Phospho-MARCKS (Ser167/170 #8722) and Phospho-JNK (Thr183/Tyr185, #9251) were obtained from Cell Signaling Technology. JNK (SC-474) antibodies were obtained from Santa Cruz. Mouse anti-Flag M2 (1:1000, Sigma) and Mouse anti-alpha tubulin (1:500, DSHB, U. of Iowa) were also used. Protein bands were visualized using secondary antibodies conjugated to HRP (1:3000, BioRad) followed by incubation with Pierce SuperSignal West Pico Chemiluminescent Substrate (Thermo Fisher Scientific, Rockford, Ill.) and analyzed using the G:BOX gel documentation system (Syngene). Tetradecanoylphorbol acetate (TPA #4174) was obtained from Cell Signaling Technology, and used at 200 nM for 20-30 mins.

Results

Example 1

Identification of GNAQ Somatic Variant. To test the hypothesis that SWS is associated with a somatic mosaic mutation, we sequenced the whole genomes of paired DNA samples from affected regions (biopsied PWS or hemispherectomized brain tissue) and matched, presumed normal regions (blood, skin, or brain) from three individuals with SWS. This resulted in the identification of 1,294 somatic SNVs found in at least one of three affected samples. We calculated the prevalence of the variant allele at each of these 1,294 sites for all affected and normal samples and identified SNVs shared between two and three affected samples (n=658), and not present in any normal samples. We functionally annotated and ranked the 1,294 somatic SNVs using VAAST. This resulted in the identification of a single non-synonymous candidate SNV supported by reads present in all three affected samples and not the presumed normal samples, a c.548G>A nucleotide transition in GNAQ on chromosome 9q21, encoding guanine nucleotide binding protein (G protein), q polypeptide. The variant is predicted to result in the amino-acid substitution p.Arg183Gln. The affected arginine residue, at position 183, is conserved in 24 human genes paralogous to Gα.

Example 2

Detection of Gnaq C.548G>A Somatic Variant in SWS Samples. A collection of tissues composed of PWS and visibly normal skin from subjects with SWS (n=23 samples from 10 subjects), apparently non-syndromic PWS and visibly normal skin from subjects without SWS (n=14 samples from 13 subjects), brain from individuals with SWS (n=50 from 18 subjects), or control brain from presumably normal individuals (n=6 from 6 subjects) was obtained from research subjects or from the NICHD Brain and Tissue Bank for Developmental Disorders. Amplicon sequencing and single-base extension interrogation (SNaPshot analysis) were used to interrogate each tissue sample for the c.548G>A mutation. SNaPshot specificity was assayed by testing five normal brain controls (data not shown). For subjects having biological or technical replicates, we call the subject positive for the mutation if at least one tissue sample tested positive (>=1% mutant allele), and negative if every tissue sample tested negative for the mutation (<1% mutant allele). 100% (9/9) of subjects with SWS were positive for the c.548G>A mutation in PWS skin tissue. 85.7% (6/7) of subjects with SWS were negative in visibly normal skin samples. 92.3% (12/13) of subjects with apparently non-syndromic PWS were positive for the mutation in PWS skin samples (Table 3). 83.3% (15/18) of subjects with SWS were positive for the c.548G>A mutation in brain samples. 100% of normal brain samples from 6/6 subjects from the control population were negative. 100% (4/4) of formalin-fixed, paraffin-embedded CCM brain samples from subjects with cerebral cavernous malformation (CCM) were negative (Table 4). 99.3% (664/669) of exomes from the 1000 Genomes database were negative. For amplicon sequencing, mutant allele frequencies ranged from 1 to 18.1%, and read depth ranged from 2,446 to 93,008, median 12,947. 1000 Genomes exome mutant allele frequencies ranged from 1 to 1.5%, and read depth ranged from 100 to 453, median 271. GNA11 mutations have also been found in uveal melanoma. We tested GNAQ Arg183Gln mutation-negative SWS and PWS samples for the presence of previously identified GNA11 mutations (p.Arg183Cys, c.547C>T and c.546C>T; p.Arg183His, c.548G>A; p.Gln209Leu, c.626A>T and c.627G>A; p.Gln209Pro, c.626A>C) using SNaPshot analysis. We did not detect any of these mutations (data not shown).

TABLE 3

Summary of somatic mutation of GNAQ in skin samples.

| ID | Mutation | PWS | SWS | Mutant Allele Frequency (%) | Samples |
|----|----------|-----|-----|-----------------------------|---------|
| 1  | Y | Y | Y | 3.60       | 1 |
| 1  | N | N | Y | 0.11       | 1 |
| 2  | Y | Y | Y | 3.17       | 1 |
| 2  | N | N | Y | 0.13       | 1 |
| 3  | Y | Y | Y | 6.06-6.46  | 2 |
| 3  | N | N | Y | 0.62-0.93  | 2 |
| 4  | Y | Y | Y | 3.50-4.51  | 2 |
| 4  | N | N | Y | 0.13-0.90  | 2 |
| 5  | Y | Y | Y | 3.38       | 1 |
| 5  | N | N | Y | 0.11       | 1 |
| 6  | Y | Y | Y | 3.99       | 1 |
| 7  | Y | Y | Y | 2.00-2.16  | 3 |
| 7  | N | N | Y | 0.09       | 1 |
| 8  | Y | Y | Y | 4.08       | 1 |
| 8  | N | N | Y | 0.06       | 1 |
| 9  | Y | Y | N | 5.58       | 1 |
| 10 | Y | Y | N | 2.76       | 1 |
| 10 | Y | N | N | 1.14       | 1 |
| 11 | Y | Y | N | 6.70       | 1 |
| 12 | N | Y | N | 0.00       | 1 |
| 13 | Y | Y | N | 5.90       | 1 |
| 14 | Y | Y | N | 6.20       | 1 |
| 15 | Y | Y | N | 14.20      | 1 |
| 16 | Y | Y | N | 1.70       | 1 |
| 17 | Y | Y | N | 4.50       | 1 |
| 18 | Y | Y | N | 5.30       | 1 |
| 19 | Y | Y | N | 4.70       | 1 |
| 20 | Y | Y | N | 4.30       | 1 |
| 21 | Y | Y | N | 18.10      | 1 |
| 22 | Y | Y | Y | 5.00       | 1 |

Data are shown for c.548G > A which results in the p.Arg183Gln amino acid substitution. This position corresponds to position 80,412,493 on chromosome 9 (NCBIv37).

Abbreviations:

ID, individual identifier;

Mutation denotes whether the p.Arg183Gln substitution is present (i.e., the mutant allele frequency is above 1%);

PWS, port-wine stain;

SWS, Sturge-Weber syndrome;

% Mutant Allele, percent mutant allele divided by total alleles (ranges for representations of multiple samples);

Samples, number of replicate samples assayed. Samples from non-syndromic PWS (PWS-Y, SWS-N), PWS from an individual with SWS (PWS-Y, SWS-Y), or normal tissue from an individual with SWS (PWS-N, SWS-Y). The p.Arg183Gln substitution was considered to be present if the mutant allele frequency was more than 1%. The mutant allele frequency was calculated as the percentage of mutant alleles divided by total alleles (with ranges shown in the case of multiple samples).

TABLE 4

Summary of somatic mutation of GNAQ in brain samples.

| ID | Mutation | SWS | % Mutant Allele | Samples |
|----|----------|-----|-----------------|---------|
| 7  | Y | Y | 5.57-5.63 | 2 |
| 23 | Y | Y | 5.56-5.78 | 2 |
| 24 | Y | Y | 2.67-3.51 | 2 |
| 25 | N | Y | 0.02-0.10 | 2 |
| 26 | Y | Y | 0.13-3.06 | 4 |
| 27 | Y | Y | 2.19-5.12 | 2 |
| 28 | Y | Y | 6.95-8.13 | 4 |
| 29 | Y | Y | 6.04-11.15 | 5 |
| 30 | Y | Y | 4.14 | 1 |
| 31 | Y | Y | 4.78 | 1 |
| 32 | Y | Y | 0.22-1.48 | 4 |
| 33 | Y | Y | 4.04-5.74 | 2 |
| 34 | N | Y | 0.05-0.12 | 2 |
| 35 | Y | Y | 0.05-1.51 | 7 |
| 36 | Y | Y | 0.35-6.03 | 5 |
| 37 | Y | Y | 5.74-6.49 | 2 |
| 38 | N | Y | 0.03-0.05 | 2 |
| 39 | Y | Y | 1.83 | 1 |
| 40 | N | N | 0.11 | 1 |
| 41 | N | N | 0.05 | 1 |
| 42 | N | N | 0.08 | 1 |
| 43 | N | N | 0.09 | 1 |
| 44 | N | N | 0.04 | 1 |
| 45 | N | N | 0.04 | 1 |
| 46 | N | CCM | 0.00 | 1 |
| 47 | N | CCM | 0.00 | 1 |
| 48 | N | CCM | 0.00 | 1 |
| 49 | N | CCM | 0.00 | 1 |

Data are shown for c.548G > A which results in the p.Arg183Gln amino acid substitution. Abbreviations are as described in Table 1.

CCM = cerebral cavernous malformation.

Samples were from individuals with SWS (SWS-Y), normal controls (SWS-N) or with CCM.

Example 3

Figure 2A:
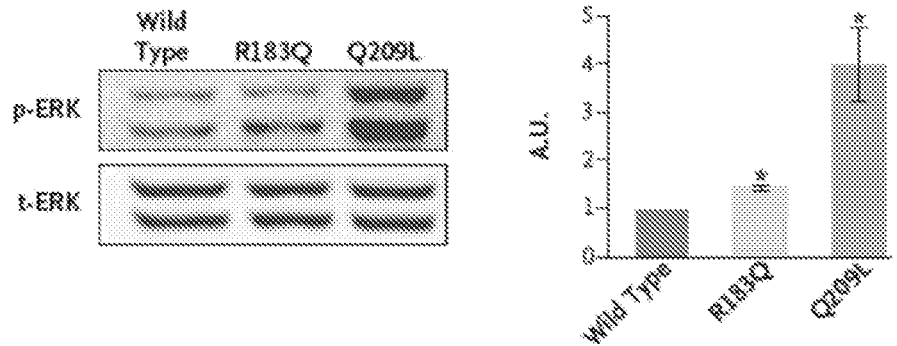
FIG. 2: Downstream effectors of GNAQ. Wild-type GNAQ, p.Arg183Gln and p.Gln209Leu were transfected into HEK 293T cells. (A) Strongly increased phosphorylation of ERK is seen with the GNAQ p.Gln209Leu and weaker but statistically significant activation with GNAQ p.Arg183Gln. (B) Increased phosphorylation of p38 with GNAQ p.Gln209Leu is seen but not with GNAQ p.Arg183Gln. (C) Increased phosphorylation of JNK is seen with GNAQ p.Gln209Leu and weaker activation with GNAQ p.Arg183Gln. (D) No change in phosphorylation of AKT is seen with either the GNAQ p.Arg183Gln or p.Gln209Leu constructs. (E) Control for transfection efficiency showing comparable amounts of the three transfected, FLAG-tagged proteins were transfected into HEK 293T cells. (F) SRE luciferase assay. Relative luciferase activity expressed under the control of the SRE promoter, coexpressed with GNAQ p.Arg183Gln' p.Gln209Leu, or wild-type constructs. (*$p<0.05$) (†$p=0.052$) Abbreviations: A.U—arbitrary units.
Figure 2B:
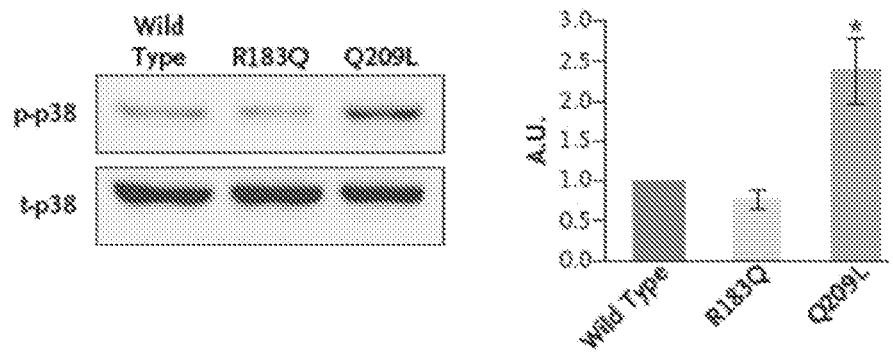
Figure 2C:
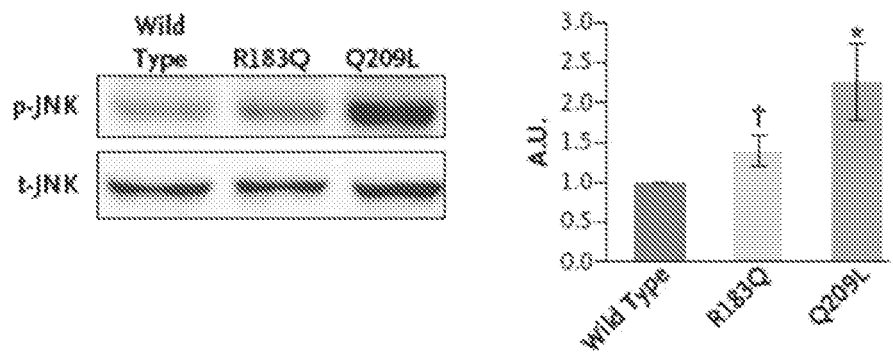
Figure 2D:
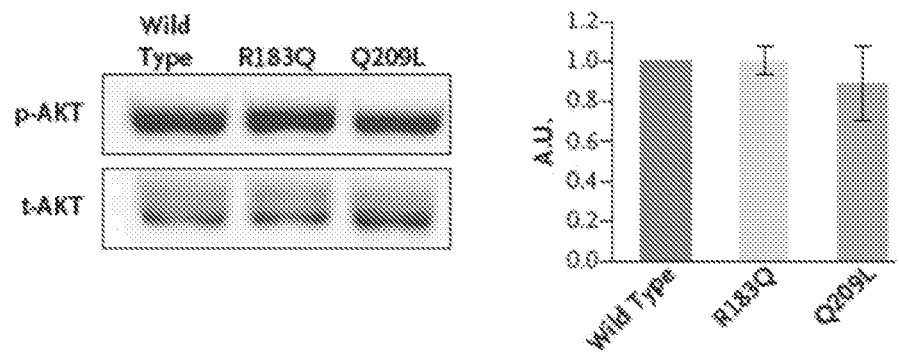
Figure 2E:
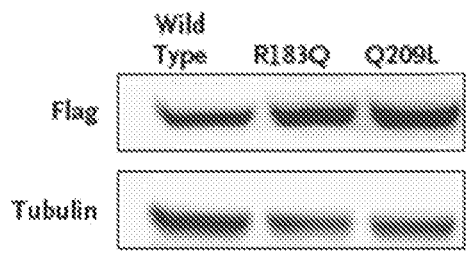

Effect of Mutation on MAPK Signaling Pathway. The somatic amino-acid substitutions GNAQ p.Gln209Leu and GNAQ p.Arg183Gln are found in uveal melanoma. The more common p.Gln209Leu has been shown to hyperactivate the MAP kinase pathway. We therefore examined whether p.Arg183Gln would likewise hyper-activate the MAP kinase pathway. As shown in FIG. 2A, when compared with cells transfected with non-mutant GNAQ, both p.Gln209Leu and p.Arg183Gln induced a significant activation of ERK. ($p<0.05$). However, the activation induced by p.Arg183Gln was modest compared to p.Gln209Leu. We also examined the effect of these substitutions on additional downstream signaling pathways. Neither substitution showed an effect on the AKT signaling pathway. p.Gln209Leu strongly activated p38 and JNK, other MAPK pathway members, while p.Arg183Gln did not (FIG. 2B,C). These data show that p.Arg183Gln represents a gain-of-function that activates downstream signaling pathways. However, when compared to the common substitution p.Gln209Leu found in uveal melanoma tissue, the effect of p.Arg183Gln in MAPK signal transduction appeared to be both weaker and less promiscuous in its activation of downstream effectors.

Example 4

Figure 2F:
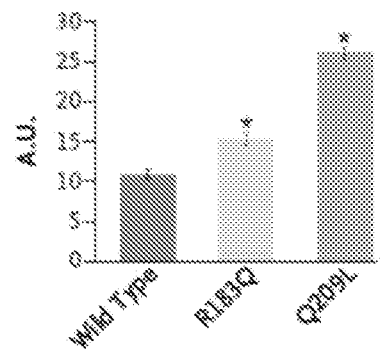
Figure 3:
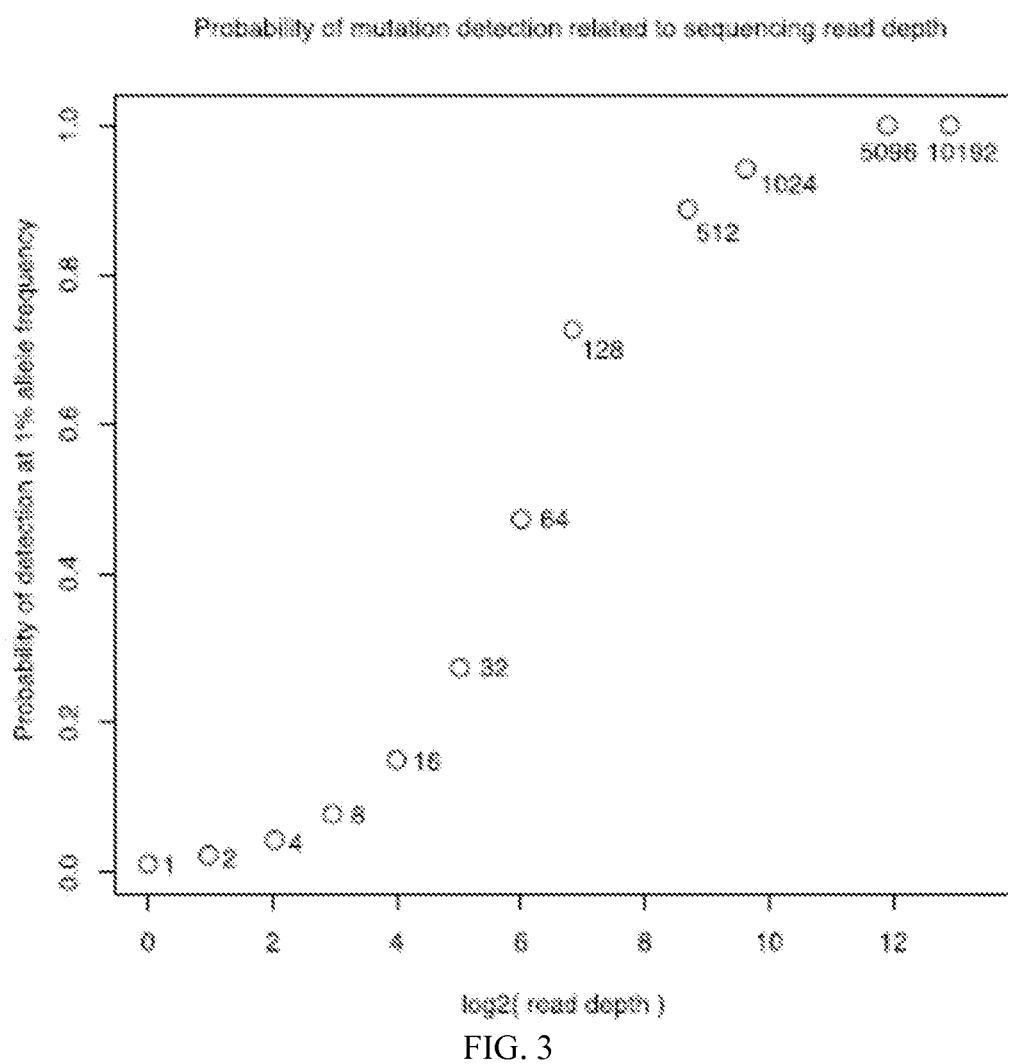
FIG. 3: Simulation of variant detection and resulting detection probabilities at varying read depth. Simulation was performed using 1,000,000 draws from an allele pool with 1% mutant allele frequency at read depths from 1 to 10,192 using a detection threshold for genotype determination of 0.5% mutant allele.

Effect of Gnaq Mutation on SRE Promoter Activity. A different substitution in GNAQ at the same amino acid residue, p.Arg183Cys, had previously been shown to hyperstimulate the serum response element (SRE) in a promoter reporter assay. We investigated whether the p.Arg183Gln substitution had the same stimulatory effect on SRE promoter activity. We transfected 293T cells with pSRE-Luc, pSV40-RL (reporter constructs) and either GNAQ, GNAQ p.Arg183Gln, or GNAQ p.Gln209Leu plasmids, and measured luciferase activity after 24 hours. Both p.Gln209Leu and p.Arg183Gln showed significantly increased reporter activity over non-mutant GNAQ ($p<0.05$), confirming that the p.Arg183Gln mutation is a gain-of-function/activating mutation (FIG. 2F). In this assay, the p.Gln209Leu substitution again showed a stronger effect than p.Arg183Gln.

Discussion

Rudolf Happle first suggested that sporadic asymmetric and/or scattered birth defects involving the skin are caused by somatic mosaic mutations that would be lethal if occurring in very early embryonic development. Somatic mosaic activating mutations have been identified in several disorders including the McCune-Albright syndrome and the *Proteus* syndrome. In the present study, we report that a specific somatic mosaic activating mutation in GNAQ is associated with both the neurocutaneous disorder Sturge-Weber syndrome and apparently non-syndromic port-wine stains. GNAQ encodes a member of the q class of G-protein alpha subunits mediating signals between G-protein-coupled receptors (GPCRs) and downstream effectors. We have identified somatic mosaic GNAQ p.Arg183Gln amino acid substitutions in both SWS and PWS, and have shown that this mutation, much like GNAQ p.Gln209Leu, activates downstream MAP kinase signaling. GNAQ Arg183 is conserved in the GTP binding pocket of all human $G\alpha$ subunits, where it plays a critical role in the hydrolysis of GTP, the key step required for inactivation of the protein. Substitution of cysteine at this position leads to a reduction in the intrinsic GTPase activity, leading to increased signaling activity.

Activating mutations in genes encoding $G_\alpha$ subunits have been previously associated with relevant phenotypes including McCune-Albright syndrome, which presents with skeletal abnormalities and abnormal skin pigmentation. Activating somatic GNAQ mutations have been identified in blue nevi and the more extensive nevus of Ota. The appearance of these melanocytic naevi, when co-localized with PWS, is termed phakomatosis pigmentovascularis (PPV), and is occasionally found in association with SWS. Mutations in GNAQ were also identified in a chemical mutagenesis screen for a dark-skin phenotype in laboratory mice. Two of the dark-skin mutant alleles were identified at positions corresponding to human GNAQ p.Val179Met and p.Phe335Leu. These germline amino acid substitutions cause an increase in the number of neural crest cells that differentiate into melanoblasts. The abnormal early melanocytic development resulting from these mutations in the neural crest cells is mediated through the G protein-coupled receptor (GPCR) endothelin. Endothelin also has important roles in vasculogenesis, and therefore dysregulation of this GPCR secondary to the GNAQ p.Arg183Gln mutation in SWS and non-syndromic PWS may also bring about vascular malformation.

A somatic activating mutation may have oncogenic potential. In fact, somatic mutations of GNAQ in melanocytes are associated with uveal melanoma. The most common mutation, GNAQ p.Gln209Leu, is an activating mutation that leads to increased downstream signaling through the MAP kinase pathway. The activation of this pathway increases cell proliferation and inhibits apoptosis. A few uveal melanomas have been reported to harbor somatic GNAQ p.Arg183Gln, although the functional consequence of this substitution has not been reported. The pathogenesis of uveal melanoma is likely to be very different from non-syndromic port-wine stains and Sturge-Weber syndrome. Melanomas are frequently found to have several somatic mutations. We find no evidence of accumulating mutations in our three paired whole genome sequences from affected and unaffected tissue from subjects with SWS. In addition, SWS, PWS, and melanocytic naevi are thought to originate during fetal development; therefore the effects of the same GNAQ somatic mutation may be quite different depending on the cell type and the point in development at which they arise. There are reported cases of uveal melanoma associated with PPV, and it is possible that the coincidence of the blue nevus and PWS phenotype in a SWS patient may indicate an increased risk for onset of uveal melanoma, although such coincidences are rare.

We have shown that the $G\alpha_q$ p.Arg183Gln substitution can activate ERK and does not activate p38 or JNK in the same fashion as p.Gln209Leu. We propose that the moderate activation of ERK and/or differential effect on p38 and JNK pathways may contribute to the PWS and syndromic characteristics of SWS. This may occur through either upstream regulation of $G\alpha_q$ or downstream modulation of the GPCR mediated signaling cascade. To provide insight into possible mechanisms underlying the partial activation of $G\alpha$ downstream signaling, we consider an interesting corollary in other $G\alpha$ proteins. The RGS (Regulator of G protein signaling) proteins serve as GTPase-activating proteins (GAPs) for Gα proteins, inhibiting downstream activation. Of these, RGS4 regulates $G\alpha_q$ and $G\alpha_i$, while RGS2 is selective for $G\alpha_q$. Upon examination of the ability of RGS4 to regulate $G\alpha_{i1}$ with activating mutations in positions p.Arg178Cys and p.Gln204Leu, homologous to $G\alpha_q$ p.Arg183Gln and p.Gln209Leu, it was found that all regulatory ability was lost for p.Gln204Leu, while GTPase activity was partially maintained for p.Arg178Cys. Thus the weaker and less promiscuously activating effects of GNAQ p.Arg183Gln, when compared to GNAQ p.Gln209Leu, may be a result of partial regulation by a member of the RGS family. Gαq is also able to initiate sustained RhoA and Rac1 activation independently of PLC-β, via direct interaction with Trio, a guanine nucleotide exchange factor (GEF). It was shown that $G\alpha_q$-mediated oncogenic proliferation, mediated through p38 and JNK, was reduced significantly following Trio knockdown without affecting PLC or ERK activation levels. This provides a possible mechanism, related to altered affinity of protein-protein interactions with both regulators (RGS family) and cascade activators (Trio), to explain the non-oncogenic proliferation seen in SWS/PWS. We hypothesize that only the weaker effect of somatic GNAQ p.Arg183Gln would be compatible with the abnormal but non-lethal development of the cerebrovascular system seen in SWS. We also hypothesize that during embryonically vulnerable periods, moderately increased baseline signaling downstream of $G\alpha_q$, and/or dysregulated signaling via GPCRs such as endothelin, may result in malformed, progressively dilated, and abnormally innervated PWS blood vessels. There is some evidence in the literature to support this hypothesis. Shirazi et al. reported the localization of phosphorylated ribosomal protein S6 (RPS6), which is downstream of MAPK signaling, to endothelial cells lining the lumenal wall of abnormal blood vessels in PWS tissue from patients with SWS.

The non-syndromic PWS may represent a late origin of the somatic GNAQ mutation in a vascular endothelial cell, whereas the SWS mutation may occur earlier in development in a progenitor cell that is a precursor to a larger variety of cell types and tissues, leading to the syndromic phenotype. Mutation during early development might lead to SWS, whereas the same mutation arising later in development might lead to the isolated, non-syndromic PWS. We observe that 0.7% (5/669) of samples of blood from the 1000 Genomes database assayed for the GNAQ p.Arg183Gln mutation were positive. The reported prevalence of PWS is 0.3-0.5%. We hypothesize therefore that the 0.7% prevalence in this database represents the occurrence of PWS in this population.

Our data unify the underlying mechanism of SWS and PWS and add a molecular basis to a decades-old hypothesis on the etiology of these malformations. The scientific and translational novelty of this discovery lies in associating both apparently non-syndromic port-wine stains and Sturge-Weber syndrome with a mutation in a specific gene, a specific genetic mechanism and a set of potential pathways, thereby providing foundation for further scientific and clinical research.

TABLE 5

Mutation Positive

| Samples | Forward Mutant Allele % | Reverse Mutant Allele % | Type of Sample | Other |
|---|---|---|---|---|
| 2P | 2.90 | 4.84 | PWS, SWS | Same as 33P* |
| 8P | 0.74 | 11.01 | PWS | |
| 8F | 4.36 | 40.94 | PWS | |
| 20P | 3.67 | 5.02 | PWS, SWS | Same as 11P* |
| 33P | 4.31 | 5.28 | PWS, SWS | Same as 2P* but different specimen |

Legend:
IH—Infantile Hemangioma;
PWS—port wine stains;
SWS—Sturge Weber Syndrome;
CH—Congenital Hemangioma;
PS—Proteus Syndrome;
LM—Lmphatic Malformation;
HFM—hamartomatous fibroadipose hypertrophy;
MS—mafucci syndrome;
Sch—spindle cell hemangioma;
dermal dendritic melanosis;
*Different specimen

TABLE 6

Mutation Negative

| Sample | Type of Sample | Other |
|---|---|---|
| 1P | PTEN mutation | Associated w/ vascular anomaly |
| 3P/3F | KTS | |
| 4P/4F | Capillary malformation | Not PWS |
| 5P | AVM w/ reactive capillary proliferation | Same as 15P* |
| 6P/6F | Vascular malformation associated w/ ddm | rare phakomatosis vascularis |
| 9F | PWS | |
| 10P/10F | Non-Involuting CH | |
| 12F | IH | |
| 13F | LM, possible PS | 23F* |
| 14F | PS | Hfh w/ overlying epidermal nevus |
| 15P | AVM | Same as 5P* |
| 16P | Dermal melanosis | |
| 19F | KTS | |
| 21F | KTS | |
| 22F | PWS | |
| 23F | LM, PS | Same 13P and F* |
| 25P | AVM | |
| 27F | KTS | |
| 29F | KTS | |
| 31P | KTS | |
| 32P | Sch | in patient with MS |
| 34P | Segmental IH | |
| 7P | Angiokeratoma | |
| 11P | Normal esophageal tissue | Same as 20P* with SWS |
| 12P | IH | |
| 13P | LM | Proteus Syndrome |
| 17P | KTS | |
| 18P | KTS | |

Above is data from a large number of vascular anamolies which were tested in a blinded fashion for the mutation in GNAQ. From these two tables can be seen that only the Sturge-Weber syndrome and port-wine birthmark tissue samples were positive for the GNAQ mutation. This data provides additional support for the specificity of the mutation causing SWS and PWB; this mutation is not linked with the other numerous vascular malformations and anamolies listed above.

We claim:

1. A method for identifying a human patient as having or likely to have Sturge-Weber syndrome (SWS) comprising the steps of:
   a. providing a nucleic acid sample from the human patient;
   b. detecting the somatic mutation c.548G>A in the guanine nucleotide-binding protein G subunit alpha (GNAQ) gene in the nucleic acid sample, wherein the detecting step comprises (i) amplicon sequencing of a polymerase chain reaction amplicon generated using the primers set forth in SEQ ID NOS:14-15 and optionally the primers set forth in SEQ ID NOS:16-17, or (ii) polymerase chain reaction and a single base pair extension assay using a primer set forth in SEQ ID NO:3 or SEQ ID NO:4; and
   c. identifying the human patient having the somatic mutation c.548G>A as having or likely to have SWS.

2. A method for monitoring treatment of a human patient with Sturge-Weber syndrome (SWS) comprising the steps of:
   a. providing a sample from the human patient undergoing treatment;
   b. detecting the number of alleles in the sample comprising the somatic mutation c.548G>A in the guanine nucleotide-binding protein G subunit alpha (GNAQ) gene or p.R183Q in the GNAQ protein, wherein the mutation is detected by (i) amplicon sequencing of a polymerase chain reaction amplicon generated using the primers set forth in SEQ ID NOS:14-15 and optionally the primers set forth in SEQ ID NOS:16-17, or (ii) polymerase chain reaction and a single base pair extension assay using a primer set forth in SEQ ID NO:3 or SEQ ID NO:4;

c. comparing the number of alleles comprising the somatic mutation to the number of alleles comprising the somatic mutation from the human patient sample provided prior to undergoing treatment; and d. determining that the human patient is improving if there is a decrease in the number of alleles comprising the somatic mutation from the sample of step (a).

3. A method to monitor progress of SWS treatment in a human patient comprising (a) detecting in a test sample relative to normal sample, a somatic mutation at c.548G>A in the GNAQ gene, wherein the detecting step comprises (i) amplicon sequencing of a polymerase chain reaction amplicon generated using the primers set forth in SEQ ID NOS: 14-15 and optionally the primers set forth in SEQ ID NOS:16-17, or (ii) polymerase chain reaction and a single base pair extension assay using a primer set forth in SEQ ID NO:3 or SEQ ID NO:4; (b) repeating one or more times the detecting step; and (c) identifying an increase, decrease or stable level of the mutation in the test sample over time.

4. A method for monitoring the response of a human patient with SWS to therapy comprising the steps of:
a. administering a therapy to the human patient;
b. obtaining a nucleic acid sample from the human patient; and
c. detecting a somatic mutation at c.548G>A of the GNAQ gene, wherein the detecting step comprises (i) amplicon sequencing of a polymerase chain reaction amplicon generated using the primers set forth in SEQ ID NOS:14-15 and optionally the primers set forth in SEQ ID NOS:16-17, or (ii) polymerase chain reaction and a single base pair extension assay using a primer set forth in SEQ ID NO:3 or SEQ ID NO:4.

5. A method for monitoring treatment of a human patient with Klippel-Trenaunay-Weber Syndrome (KTWS) comprising the steps of:
a. providing a sample from the human patient undergoing treatment;
b. detecting the number of alleles in the sample comprising the somatic mutation c.548G>A in the guanine nucleotide-binding protein G subunit alpha (GNAQ) gene, wherein the detecting step comprises (i) amplicon sequencing of a polymerase chain reaction amplicon generated using the primers set forth in SEQ ID NOS: 14-15 and optionally the primers set forth in SEQ ID NOS:16-17, or (ii) polymerase chain reaction and a single base pair extension assay using a primer set forth in SEQ ID NO:3 or SEQ ID NO:4;
c. comparing the number of alleles comprising the somatic mutation to the number of alleles comprising the somatic mutation from the human patient sample provided prior to undergoing treatment; and
d. determining that the human patient is improving if there is a decrease in the number of alleles comprising the somatic mutation from the sample of step (a).

6. A method to monitor progress of KTWS treatment in a human patient comprising (a) detecting in a test sample relative to normal sample, a somatic mutation at c.548G>A in the GNAQ gene, wherein the detecting step comprises (i) amplicon sequencing of a polymerase chain reaction amplicon generated using the primers set forth in SEQ ID NOS: 14-15 and optionally the primers set forth in SEQ ID NOS:16-17, or (ii) polymerase chain reaction and a single base pair extension assay using a primer set forth in SEQ ID NO:3 or SEQ ID NO:4; (b) repeating one or more times the detecting step; and (c) identifying an increase, decrease or stable level of the mutation in the test sample over time.

7. A method for monitoring the response of a human patient with KTWS to therapy comprising the steps of:
a. administering a therapy to the human patient;
b. obtaining a nucleic acid sample from the human patient; and
c. detecting a somatic mutation at c.548G>A of the GNAQ gene is present, wherein the detecting step comprises (i) amplicon sequencing of a polymerase chain reaction amplicon generated using the primers set forth in SEQ ID NOS:14-15 and optionally the primers set forth in SEQ ID NOS:16-17, or (ii) polymerase chain reaction and a single base pair extension assay using a primer set forth in SEQ ID NO:3 or SEQ ID NO:4.

8. A method for monitoring treatment of a human patient with Port Wine Stains (PWS) comprising the steps of:
a. providing a sample from the human patient undergoing treatment;
b. detecting the number of alleles in the sample comprising the somatic mutation c.548G>A in the guanine nucleotide-binding protein G subunit alpha (GNAQ) gene, wherein the detecting step comprises (i) amplicon sequencing of a polymerase chain reaction amplicon generated using the primers set forth in SEQ ID NOS: 14-15 and optionally the primers set forth in SEQ ID NOS:16-17, or (ii) polymerase chain reaction and a single base pair extension assay using a primer set forth in SEQ ID NO:3 or SEQ ID NO:4;
c. comparing the number of alleles comprising the somatic mutation to the number of alleles comprising the somatic mutation from a human patient sample provided prior to undergoing treatment; and
d. determining that the human patient is improving if there is a decrease in the number of alleles comprising the somatic mutation from the sample of step (a).

9. A method for prognosing or monitoring treatment of a human patient with SWS, KTWS and/or PWS comprising the steps of:
a. providing a sample from the human patient undergoing treatment;
b. detecting the number of alleles in the sample comprising a somatic mutation at c.548G>A in the guanine nucleotide-binding protein G subunit alpha (GNAQ) gene, wherein the detecting step comprises (i) amplicon sequencing of a polymerase chain reaction amplicon generated using the primers set forth in SEQ ID NOS: 14-15 and optionally the primers set forth in SEQ ID NOS:16-17, or (ii) polymerase chain reaction and a single base pair extension assay using a primer set forth in SEQ ID NO:3 or SEQ ID NO:4;
c. comparing the number of alleles comprising the somatic mutation to the number of alleles comprising the somatic mutation from the human patient sample provided prior to undergoing treatment; and
d. determining that the human patient is improving if there is a decrease in the number of alleles comprising the somatic mutation from the sample of step (a).

* * * * *

SEQUENCE LISTING

<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: GNAQ exon 4 amplicon forward primer

<400> SEQUENCE: 1
attgtgtctt ccctcctcta                                               20

<210> SEQ ID NO 2
<211> LENGTH: 20
<212> TYPE: DNA
<213> ORGANISM: Artificial Sequence
<220> FEATURE:
<223> OTHER INFORMATION: GNAW exon 4 amplicon reverse primer

<400> SEQUENCE: 2
ggtttcatgg actcagttac                                               20

<210> SEQ ID NO 3
<211> LENGTH: 24
<212> TYPE: DNA
<213> ORGANISM: Artificial Sequence
<220> FEATURE:
<223> OTHER INFORMATION: Snapshot forward primer for c.548G>A

<400> SEQUENCE: 3
cgcaacaaga tgtgcttaga gttc                                          24

<210> SEQ ID NO 4
<211> LENGTH: 17
<212> TYPE: DNA
<213> ORGANISM: Artificial Sequence
<220> FEATURE:
<223> OTHER INFORMATION: Snapshot reverse primer for c.548G>A

<400> SEQUENCE: 4
tccctgtggt ggggact                                                  17

<210> SEQ ID NO 5
<211> LENGTH: 20
<212> TYPE: DNA
<213> ORGANISM: Artificial Sequence
<220> FEATURE:
<223> OTHER INFORMATION: GNA11 exon 4 amplicon forward primer

<400> SEQUENCE: 5
gagcacccac cgctgtgttg                                               20

<210> SEQ ID NO 6
<211> LENGTH: 21
<212> TYPE: DNA
<213> ORGANISM: Artificial Sequence
<220> FEATURE:
<223> OTHER INFORMATION: GNA11 exon 4 amplicon reverse primer

<400> SEQUENCE: 6
ggcaaatgag cctctcagtg c                                             21

<210> SEQ ID NO 7
<211> LENGTH: 18
<212> TYPE: DNA
<213> ORGANISM: Artificial Sequence

```
<220> FEATURE:
<223> OTHER INFORMATION: Snapshot forward primer for c.547C>T

<400> SEQUENCE: 7
caggacgtgc tgcgggtc                                                  18

<210> SEQ ID NO 8
<211> LENGTH: 18
<212> TYPE: DNA
<213> ORGANISM: Artificial Sequence
<220> FEATURE:
<223> OTHER INFORMATION: Snapshot reverse primer for c.547C>T

<400> SEQUENCE: 8
tgccggtggt gggcacgc                                                  18

<210> SEQ ID NO 9
<211> LENGTH: 18
<212> TYPE: DNA
<213> ORGANISM: Artificial Sequence
<220> FEATURE:
<223> OTHER INFORMATION: Snapshot forward primer for c.546C>T

<400> SEQUENCE: 9
gcaggacgtg ctgcgggt                                                  18

<210> SEQ ID NO 10
<211> LENGTH: 18
<212> TYPE: DNA
<213> ORGANISM: Artificial Sequence
<220> FEATURE:
<223> OTHER INFORMATION: Snapshot forward primer for c.548G>A

<400> SEQUENCE: 10
aggacgtgct gcgggtcc                                                  18

<210> SEQ ID NO 11
<211> LENGTH: 18
<212> TYPE: DNA
<213> ORGANISM: Artificial Sequence
<220> FEATURE:
<223> OTHER INFORMATION: Snapshot reverse primer for c.548G>A

<400> SEQUENCE: 11
atgccggtgg tgggcacg                                                  18

<210> SEQ ID NO 12
<211> LENGTH: 2215
<212> TYPE: DNA
<213> ORGANISM: Homo sapiens

<400> SEQUENCE: 12
gggagggtgt gtgtgcgcgc tgtgagcagg gggtgccggc ggggctgcag cggaggcact    60
ttggaagaat gactctggag tccatcatgg cgtgctgcct gagcgaggag gccaaggaag   120
cccggcggat caacgacgag atcgagcggc agctccgcag ggacaagcgg gacgcccgcc   180
gggagctcaa gctgctgctg ctcgggacag gagagtgg caagagtacg tttatcaagc     240
agatgagaat catccatggg tcaggatact ctgatgaaga taaaaggggc ttcaccaagc   300
tggtgtatca gaacatcttc acggccatgc aggccatgat cagagccatg gacacactca   360 agatccccata caagtatgag cacaataagg ctcatgcaca attagttcga gaagttgatg   420
tggagaaggt gtctgctttt gagaatccat atgtagatgc aataaagagt ttatggaatg   480
```

-continued

| | |
|---|---|
| atcctggaat ccaggaatgc tatgatagac gacgagaata tcaattatct gactctacca | 540 |
| aatactatct taatgacttg gaccgcgtag ctgaccctgc ctacctgcct acgcaacaag | 600 |
| atgtgcttag agttcgagtc cccaccacag ggatcatcga ataccccttt gacttacaaa | 660 |
| gtgtcatttt cagaatggtc gatgtagggg gccaaaggtc agagagaaga aaatggatac | 720 |
| actgctttga aaatgtcacc tctatcatgt ttctagtagc gcttagtgaa tatgatcaag | 780 |
| ttctcgtgga gtcagacaat gagaaccgaa tggaggaaag caaggctctc tttagaacaa | 840 |
| ttatcacata ccccctggtt cagaactcct cggttattct gttcttaaac aagaaagatc | 900 |
| ttctagagga gaaaatcatg tattcccatc tagtcgacta cttcccagaa tatgatggac | 960 |
| cccagagaga tgcccaggca gcccgagaat tcattctgaa gatgttcgtg gacctgaacc | 1020 |
| cagacagtga caaattatc tactcccact tcacgtgcgc cacagacacc gagaatatcc | 1080 |
| gctttgtctt tgctgccgtc aaggacacca tcctccagtt gaacctgaag gagtacaatc | 1140 |
| tggtctaatt gtgcctccta cacacccgcc ctgcccttcc ctggtgggct attgaagata | 1200 |
| cacaagaggg actgtatttc tgtggaaaac aatttgcata atactaattt attgccgtcc | 1260 |
| tggactctgt gtgagcgtgt ccacagagtt tgtagtaaat attatgattt tatttaaact | 1320 |
| attcagagga aaaacagagg atgctgaagt acagtcccag cacatttcct ctctatcttt | 1380 |
| tttttaggca aaaccttgtg actcagtgta ttttaaattc tcagtcatgc actcacaaag | 1440 |
| ataagacttg tttctttctg tctctctctc tttttctttt ctatggagca aaacaaagct | 1500 |
| gatttcccctt ttttcttccc ccgctaattc atacctccct cctgatgttt ttcccaggtt | 1560 |
| acaatggcct ttatcctagt tccattcttg gtcaagtttt tctctcaaat gatacagtca | 1620 |
| ggacacatcg ttcgatttaa gccatcatca gcttaattta agtttgtagt ttttgctgaa | 1680 |
| ggattatatg tattaatact tacggtttta aatgtgttgc tttggataca cacatagttt | 1740 |
| cttttttaat agaatatact gtcttgtctc actttggact gggacagtgg atgcccatct | 1800 |
| aaaagttaag tgtcatttct tttagatgtt taccttcagc catagcttga ttgctcagag | 1860 |
| aaatatgcag aaggcaggat caaagacaca caggagtcct ttcttttgaa atgccacgtg | 1920 |
| ccattgtctt tcctcccttc tttgcttctt tttcttaccc tctctttcaa ttgcagatgc | 1980 |
| caaaaaagat gccaacagac actacattac cctaatggct gctacccaga acctttttat | 2040 |
| aggttgttct taattttttt gttgttgttg ttcaagcttt tcctttcttt tttttcttgg | 2100 |
| tgtttgggcc acgattttaa aatgactttt attatgggta tgtgttgcca aagctggctt | 2160 |
| tttgtcaaat aaaatgaata cgaacttaaa aaataaaaaa aaaaaaaaaa aaaaa | 2215 |

<210> SEQ ID NO 13
<211> LENGTH: 359
<212> TYPE: PRT
<213> ORGANISM: Homo sapiens

<400> SEQUENCE: 13

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr

```
             65                  70                  75                  80
        Gln Asn Ile Phe Thr Ala Met Gln Ala Met Ile Arg Ala Met Asp Thr
                         85                  90                  95

Leu Lys Ile Pro Tyr Lys Tyr Glu His Asn Lys Ala His Ala Gln Leu
                        100                 105                 110

Val Arg Glu Val Asp Val Glu Lys Val Ser Ala Phe Glu Asn Pro Tyr
                        115                 120                 125

Val Asp Ala Ile Lys Ser Leu Trp Asn Asp Pro Gly Ile Gln Glu Cys
                    130                 135                 140

Tyr Asp Arg Arg Glu Tyr Gln Leu Ser Asp Ser Thr Lys Tyr Tyr
        145                 150                 155                 160

Leu Asn Asp Leu Asp Arg Val Ala Asp Pro Ala Tyr Leu Pro Thr Gln
                        165                 170                 175

Gln Asp Val Leu Arg Val Arg Val Pro Thr Thr Gly Ile Ile Glu Tyr
                        180                 185                 190

Pro Phe Asp Leu Gln Ser Val Ile Phe Arg Met Val Asp Val Gly Gly
                    195                 200                 205

Gln Arg Ser Glu Arg Arg Lys Trp Ile His Cys Phe Glu Asn Val Thr
        210                 215                 220

Ser Ile Met Phe Leu Val Ala Leu Ser Glu Tyr Asp Gln Val Leu Val
        225                 230                 235                 240

Glu Ser Asp Asn Glu Asn Arg Met Glu Glu Ser Lys Ala Leu Phe Arg
                        245                 250                 255

Thr Ile Ile Thr Tyr Pro Trp Phe Gln Asn Ser Ser Val Ile Leu Phe
                        260                 265                 270

Leu Asn Lys Lys Asp Leu Leu Glu Glu Lys Ile Met Tyr Ser His Leu
                    275                 280                 285

Val Asp Tyr Phe Pro Glu Tyr Asp Gly Pro Gln Arg Asp Ala Gln Ala
                    290                 295                 300

Ala Arg Glu Phe Ile Leu Lys Met Phe Val Asp Leu Asn Pro Asp Ser
        305                 310                 315                 320

Asp Lys Ile Ile Tyr Ser His Phe Thr Cys Ala Thr Asp Thr Glu Asn
                        325                 330                 335

Ile Arg Phe Val Phe Ala Ala Val Lys Asp Thr Ile Leu Gln Leu Asn
                    340                 345                 350

Leu Lys Glu Tyr Asn Leu Val
                355

<210> SEQ ID NO 14
<211> LENGTH: 70
<212> TYPE: DNA
<213> ORGANISM: Artificial Sequence
<220> FEATURE:
<223> OTHER INFORMATION: P1: Forward amplicon w/barcode
<220> FEATURE:
<221> NAME/KEY: misc_feature
<223> OTHER INFORMATION: n=any nucleotide
<220> FEATURE:
<221> NAME/KEY: misc_feature
<222> LOCATION: (34)..(44)
<223> OTHER INFORMATION: n is a, c, g, or t

<400> SEQUENCE: 14
acactctttc cctacacgac gctcttccga tctnnnnnnn nnnngggtat tcgatgatcc     60
ctgtggtggg                                                           70

<210> SEQ ID NO 15
```

```
<211> LENGTH: 61
<212> TYPE: DNA
<213> ORGANISM: Artificial Sequence
<220> FEATURE:
<223> OTHER INFORMATION: P2: Reverse amplicon

<400> SEQUENCE: 15
ctcggcattc ctgctgaacc gctcttccga tctcctttcc gtagacagct ttggtgtgat    60
g                                                                   61

<210> SEQ ID NO 16
<211> LENGTH: 58
<212> TYPE: DNA
<213> ORGANISM: Artificial Sequence
<220> FEATURE:
<223> OTHER INFORMATION: P3: Sequencing adapter 1

<400> SEQUENCE: 16
aatgatacgg cgaccaccga gatctacact ctttccctac acgacgctct tccgatct     58

<210> SEQ ID NO 17
<211> LENGTH: 61
<212> TYPE: DNA
<213> ORGANISM: Artificial Sequence
<220> FEATURE:
<223> OTHER INFORMATION: P4: Sequencing adapter 2

<400> SEQUENCE: 17
caagcagaag acggcatacg agatcggtct cggcattcct gctgaaccgc tcttccgatc    60
t                                                                   61

<210> SEQ ID NO 18
<211> LENGTH: 33
<212> TYPE: DNA
<213> ORGANISM: Artificial Sequence
<220> FEATURE:
<223> OTHER INFORMATION: P1_1: 5' fragment of SEQ ID NO:14 (P1)

<400> SEQUENCE: 18
acactctttc cctacacgac gctcttccga tct                                 33

<210> SEQ ID NO 19
<211> LENGTH: 26
<212> TYPE: DNA
<213> ORGANISM: Artificial Sequence
<220> FEATURE:
<223> OTHER INFORMATION: P1_2: 3' fragment of SEQ ID NO:14 (P1)

<400> SEQUENCE: 19
gggtattcga tgatccctgt ggtggg                                         26
```